United States Patent [19]

Beeby

[11] 4,139,618

[45] * Feb. 13, 1979

[54] CEPHALOSPORIN TYPE ANTIBACTERIALS

[75] Inventor: Philip J. Beeby, Melbourne, Australia

[73] Assignee: Syntex (U.S.A.) Inc., Palo Alto, Calif.

[*] Notice: The portion of the term of this patent subsequent to Sep. 28, 1993, has been disclaimed.

[21] Appl. No.: 700,697

[22] Filed: Jun. 28, 1976

Related U.S. Application Data

[63] Continuation-in-part of Ser. No. 605,109, Aug. 15, 1975, Pat. No. 4,049,806, and a continuation-in-part of Ser. No. 621,717, Oct. 14, 1975, Pat. No. 3,983,113, and a continuation-in-part of Ser. No. 664,599, Mar. 8, 1976.

[51] Int. Cl.$^2$ ............................................. C07D 501/36
[52] U.S. Cl. ..................................... 424/246; 544/26; 544/27
[58] Field of Search ................ 260/243 C; 544/26, 27

[56] References Cited

U.S. PATENT DOCUMENTS

| | | | |
|---|---|---|---|
| 3,516,997 | 6/1970 | Takano et al. | 260/243 C |
| 3,983,113 | 9/1976 | Beeby | 260/243 C |
| 4,013,650 | 3/1977 | Fechtig | 260/243 C |
| 4,016,159 | 4/1977 | Bormann et al. | 260/243 C |

*Primary Examiner*—Nicholas S. Rizzo
*Attorney, Agent, or Firm*—Richard J. Hammond; Gerard A. Blaufarb

[57] ABSTRACT

3-[3-(methyl-1,3,4-thiadiazol-5-ylthio)-prop-1-(t)-enyl]-7β-(α-substituted acetamido)-ceph-3-em-4-carboxylic acids; 3-[3-(3-methyl-1,2,4-thiadiazol-5-ylthio)-prop-1-(t)-enyl]-7β-(α-substituted acetamido)-ceph-3-em-4-carboxylic acids; and 3-[3-(2-methyl-1,3,4-oxadiazol-5-ylthio)-prop-1-(t)-enyl]-7β-(α-substituted acetamido)-ceph-3-em-4-carboxylic acids and derivatives and salts thereof and processes for preparing such compounds. The compounds are useful as antibacterials and are active against a wide variety of gram positive and gram negative bacteria.

59 Claims, No Drawings

CEPHALOSPORIN TYPE ANTIBACTERIALS

CROSS REFERENCE TO RELATED APPLICATIONS

This application is a continuation-in-part of application U.S. Ser. No. 605,109, filed Aug. 15, 1975 now U.S. Pat. No. 4,049,806, application U.S. Ser. No. 621,717, filed Oct. 14, 1975 now U.S. Pat. No. 3,983,113 and application U.S. Ser. No. 664,599, filed Mar. 8, 1976.

BACKGROUND OF THE INVENTION

1. The Invention

This invention relates to cephalosporin type compounds, having antibacterial activity, and intermediates and processes for preparing such compounds. In a further aspect, this invention relates to 3-[3-(2-methyl-1,3,4-thiadiazol-5-ylthio)prop-1-(t)-enyl]-7β-(α-substituted acetamido)-ceph-3-em-4-carboxylic acids; 3-[3-(3-methyl-1,2,4-thiadiazol-5-ylthio)prop-1-(t)-enyl]-7β-(α-substituted acetamido)-ceph-3-em-4-carboxylic acids; and 3-[3-(2-methyl-1,3,4-oxadiazol-5-ylthio)prop-1-(t)-enyl]-7β-(α-substituted acetamido)-ceph-3-em-4-carboxylic acids and to esters and salts thereof; and to intermediates for, and methods of preparing such compounds. In a still further aspect, the invention relates to pharmaceutical compositions and antiseptic compositions containing such compounds and to methods of destroying and/or inhibiting the growth of gram negative and/or gram positive bacteria.

2. The Prior Art

Since the first discovery that certain derivatives of Cephalosporin C exhibit potent antibiotic activity, a large number of cephalosporin type compounds have been synthesized for possible improved, or different, antibiotic activity and selectivity (note for example, U.S. Pat. Nos. 3,769,227, 3,830,700, 3,853,860, 3,859,274, 3,864,338 and 3,867,380). A general discussion of cephalosporins can be found in *Cephalosporins and Penicillins Chemistry and Biology*, edit E. H. Flynn, Academic Press, Inc. (1972).

SUMMARY OF THE INVENTION

In summary, the compounds of the invention can be represented by the following generic formulas:

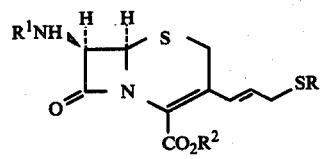

I (trans)

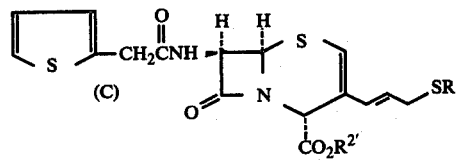

wherein:

R is 2-methyl-1,3,4-thiadiazol-5-yl, 3-methyl-1,2,4-thiadiazol-5-yl or 2-methyl-1,3,4-oxadiazol-5-yl;

$R^1$ is hydrogen or a group having the formula:

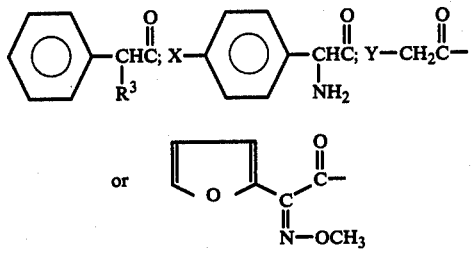

wherein $R^3$ is hydrogen, hydroxy, sulfo or carboxy; X is hydrogen or hydroxy; and Y is thiophen-2-yl, phenoxy, trifluoromethylthio, (1H)-tetrazol-1-yl, sydnon-3-yl, or cyanomethylthio;

$R^2$ is hydrogen, or a protecting group selected from the group of benzhydryl, benzyl, o-nitrobenzyl, p-nitrobenzyl, 3,5-dinitrobenzyl, p-methoxybenzyl, t-butyl, pivaloyloxymethyl, phenacyl, and polyhaloalkyl having two to six carbon atoms, e.g. 2,2,2,-trichloroethyl; and $R^{2'}$ is a protecting group selected from the same group of protecting groups as $R^2$.

The pharmaceutically acceptable salts of the above compounds, wherein $R^1$ is other than hydrogen, with respect to the C-4 acid and $R^3$-sulfo and carboxy moieties, are also encompassed within the scope of the invention. Also, as can be seen from formulas I and (C), the steric configuration of the propenyl double bond is trans and the substituent at the 7-position is beta oriented.

In summary, one process of the invention comprises:

(A) Reacting a 3-formyl-7β-(thiophen-2-yl-acetamido)-ceph-2-em-4-carboxylate ester with a vinyl Grignard reagent to yield the corresponding 3-(1-hydroxyprop-2-enyl)-7β-(thiophen-2-yl-acetamido)-ceph-2-em-4-carboxylate ester intermediate and reacting this intermediate with 5-mercapto-2-methyl-1,3,4-thiadiazole, 5-mercapto-3-methyl-1,2,4-thiadiazole or 5-mercapto-2-methyl-1,3,4-oxadiazole to yield the corresponding heterocycle-ylthioprop-1-(t)-enyl intermediate of formula (C);

(B) Rearrangement of the C-2(3) double bond of the heterocycle-ylthioprop-1-(t)-enyl intermediate of formula (C) to C-3(4) and then (i) optionally cleaving the C-4 carboxylate ester protecting group to yield the corresponding 4-carboxylic acid of formula I and optionally treating the acid with a pharmaceutically acceptable base to yield the corresponding salt; or (ii) cleaving the 7β-(thiophen-2-yl-acetamido) moiety to yield the 7β-amino intermediate of formula I ($R^1$ is H); and (C) Acylation of the 7β-amino group of the 7β-amino intermediate of formula I and hydrolysis of the 4-carboxylate ester protecting group, or vice-versa, to yield the corresponding 4-carboxylic acid of formula I, and optionally treating the acid with a pharmaceutically acceptable base to yield the corresponding salt.

In summary, a second process of the invention comprises:

(A) Treating a C-4 position protected 3-(1-hydroxyprop-2-enyl)-7β-(thiophen-2-ylacetamido)-ceph-2-em-4-carboxylate to rearrange the prop-2-enyl vinyl unsaturation to the 1(2) position and the 1-hydroxy substituent to the 3-position of the propenyl group and to transform the hydroxy group to an acetoxy group;

(B) Rearrangement of the C-2(3) double bond of the corresponding 3-(3-acetoxyprop-1-(t)-enyl)-7β-(thiophen-2-yl-acetamido)-ceph-2-em-4-carboxylate intermediate to C-3(4) and then (i) optionally cleaving the C-4 carboxylate ester protecting group to yield the corresponding 4-carboxylic acid and optionally treating the acid with a pharmaceutically acceptable base to yield the corresponding salt; or (ii) cleaving the 7β-(thiophen-2-yl-acetamido) moiety to yield the 7β-amino intermediate;

(C) Acylation of the 7β-amino group of the 7β-amino intermediate and hydrolysis of the 4-carboxylate ester protecting group, or vice-versa, to yield the corresponding 4-carboxylic acid and optionally treating the acid with a pharmaceutically acceptable base to yield the corresponding salt; and (D) Treating the acid or salt products of (B) and (C) above to replace the 3-acetoxy group on the prop-1-(t)-enyl substituent with 2-methyl-1,3,4-thiadiazol-5-ylthio, 3-methyl-1,2,4-thiadiazol-5-ylthio or 2-methyl-1,3,4-oxadiazol-5-ylthio to obtain the corresponding antibacterial agents of the instant invention.

In summary, the pharmaceutical compositions and antiseptic compositions of the invention, comprise the 4-carboxylic acid compounds of formula I and/or pharmaceutically acceptable salts thereof, and a pharmaceutically acceptable carrier or antiseptic carrier.

In summary, the process of the invention for reducing or inhibiting bacterial infections comprises administering an effective amount of the carboxylic acids of formula I or a pharmaceutically acceptable salt thereof, to mammals suffering from such infections, or in the case of undesired bacterial growth on inanimate objects, applying an effective amount of the aforementioned compounds in an antiseptic carrier to such objects.

FURTHER DESCRIPTION OF THE INVENTION AND PREFERRED EMBODIMENTS

The compounds of the invention can be represented by the following subgeneric formulas:

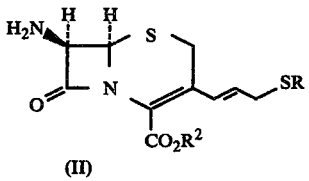
(II)

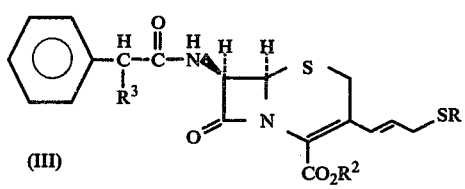
(III)

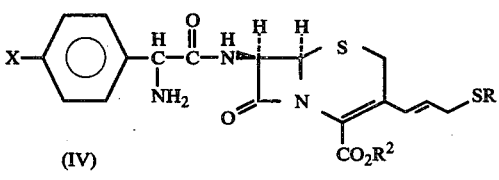
(IV)

-continued

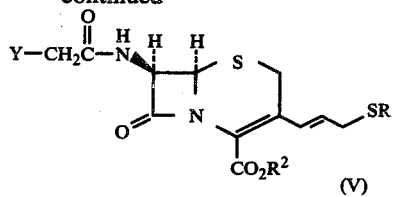
(V)

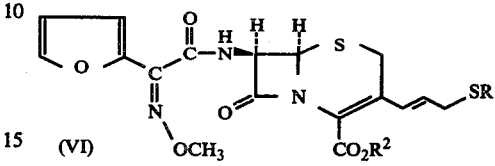
(VI)

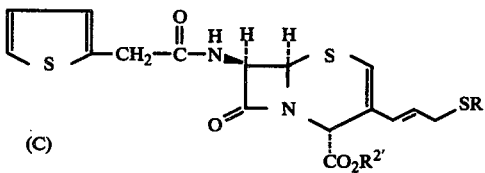
(C)

wherein

R is 2-methyl-1,3,4-thiadiazol-5-yl, 3-methyl-1,2,4-thiadiazol-5-yl or 2-methyl-1,3,4-oxadiazol-5-yl;

$R^2$ is hydrogen, or a protecting group selected from the group of benzhydryl, benzyl, o-nitrobenzyl, p-nitrobenzyl, 3,5-dinitrobenzyl, p-methoxybenzyl, t-butyl, pivaloyloxymethyl, phenacyl and polyhaloalkyl having two to six carbon atoms, e.g. 2,2,2-trichloroethyl;

$R^{2'}$ is a protecting group selected from the same group of protecting groups as $R^2$;

$R^3$ is hydrogen, hydroxy, carboxy or sulfo;

X is hydrogen or hydroxy; and

Y is thiophen-2-yl, trifluoromethylthio, phenoxy, (1H)tetrazol-1-yl, sydnon-3-yl or cyanomethylthio.

Also, encompassed within the invention are the pharmaceutically acceptable salts of compounds of formula III, IV, V and VI.

The compounds of formula III wherein $R^3$ is hydroxy, sulfo or carboxy, and the compounds of formula IV exist as optical isomers; accordingly, the above formulas are intended to represent the respective (D) and (L) optical isomers as well as mixtures thereof and the individual isomers as well as mixtures thereof are encompassed within the invention. Generally, in terms of antibiotic activity, the (D) optical isomers are preferred.

Also, as previously noted, the C-7 position amino or carbonylamino substituent is beta oriented and the propenyl double bond is trans oriented.

Preferred compounds embraced by subgeneric formulas III, IV, V and IV are those wherein R is 2-methyl-1,3,4-thiadiazol-5-yl.

Particularly preferred compounds within the group described in the previous paragraph are those compounds of formulas V and VI. Especially preferred compounds of formula V are those wherein Y is (1H)-tetrazol-1-yl or thiophen-2-yl.

Most especially preferred compounds of formulas V and VI are:

3-[3-(2-methyl-1,3,4-thiadiazol-5-ylthio)-prop-1-(t)enyl]-7β-[2-methoximino(fur-2-yl)acetamido]-ceph-3-em-4-carboxylic acid;

3-[3-(2-methyl-1,3,4-thiadiazol-5-ylthio)-prop-1-
(t)enyl]-7β-[α-(1H)-tetrazol-1-ylacetamido]-ceph-3-
em-4-carboxylic acid; and 3-[3-(2-methyl-1,3,4-thiadiazol-5-ylthio)-prop-1-
(t)enyl]-7β-(thiophen-2-ylacetamido)-ceph-3-em-4-
carboxylic acid; and the pharmaceutically acceptable
salts thereof.

III, IV, V and VI. The preferred compounds of formula
II are the corresponding precursors of the preferred,
particularly preferred and especially preferred compounds of formulas III, IV, V and VI.

One process for preparing the compounds of the
invention can be schematically represented by the following sequence of overall reaction equations.

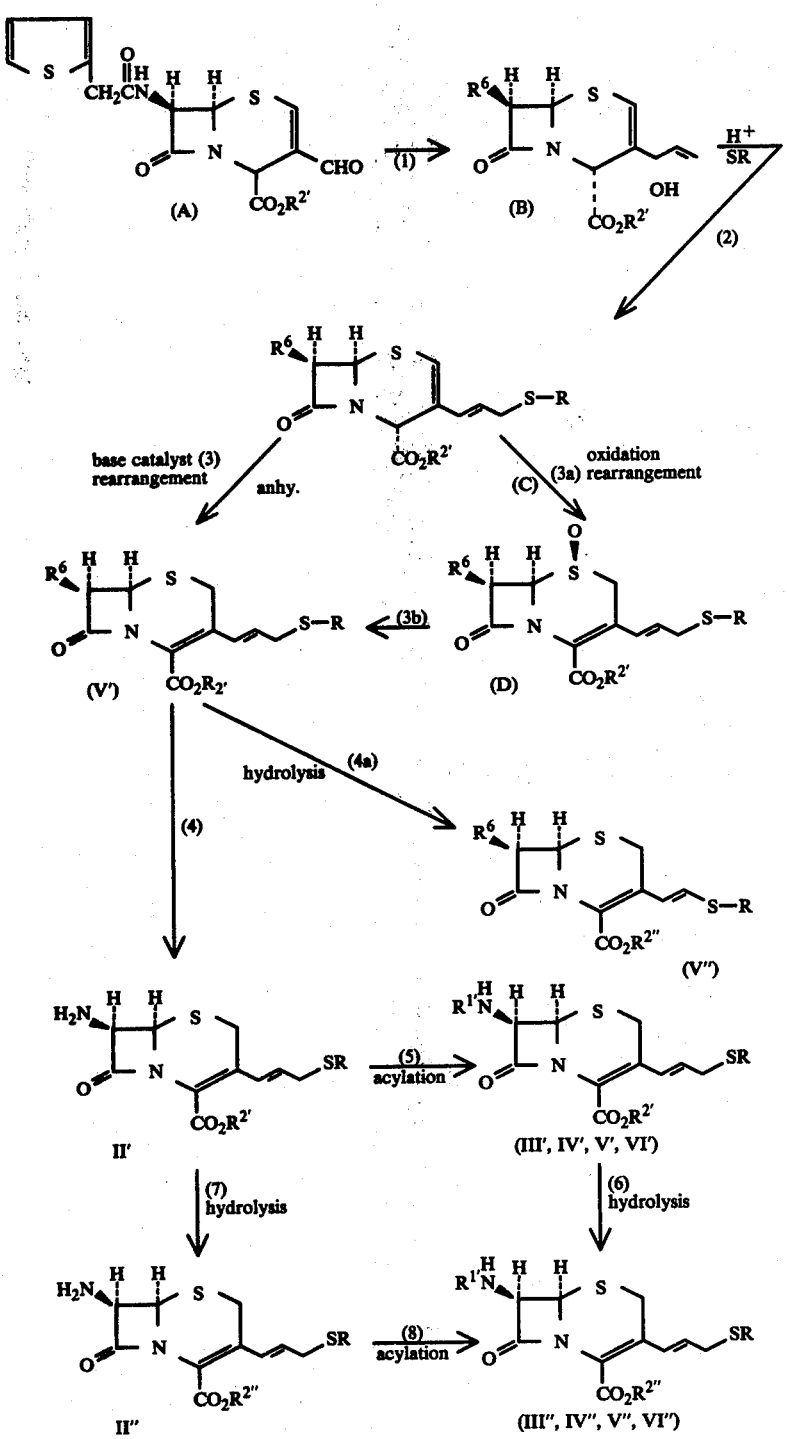

In terms of convenience, the sodium salts are preferred, correspondingly the particularly preferred salts are the sodium salts of the preferred, particularly preferred and especially preferred compounds of formulas wherein R is as defined hereinabove; $R^{1'}$ is as defined hereinabove for $R^1$, but is other than hydrogen; $R^{2'}$ is a suitable protecting group, e.g. benzhydryl; $R^{2''}$ is hydrogen or a pharmaceutically acceptable cation, e.g. sodium; $R^6$ is the group

and the ~ OH in formula B indicates a mixture of α- and β-hydroxy isomers.

Step 1, of the above process, can be conveniently effected by treating the starting material of formula A with a suitable vinyl Grignard reagent, preferably in a suitable inert organic solvent. Typically, this treatment is conducted at temperatures in the range of −100° to −20° C., preferably about from −60° to −80° C., for about from 0.25 to 2.0 hours, and preferably about from 0.25 to 0.5 hours. Typically, a mole ratio of Grignard reagent to compound of formula A of about from 3 to 10, preferably about from 4 to 5 is used. Typically, and preferably, the treatment is conducted under anhydrous conditions and under an inert atmosphere; e.g. nitrogen. Suitable inert organic solvents which can be used include, for example, tetrahydrofuran, dimethoxyethane, dioxane and the like, and mixtures thereof. Suitable Grignard reagents which can be used include, for example, vinyl magnesium chloride, vinyl magnesium bromide and the like. The resulting product is a mixture of α- and β-hydroxy isomers which, if desired, can be resolved by conventional procedures.

The starting materials of formula A are known compounds and can be prepared according to known procedures such as, for example, described in U.S. Pat. No. 3,864,338, and in the Preparations set forth hereinbelow; or by obvious modifications of such procedures; e.g. by substitution of protecting groups.

Step 2, of the process, can be conveniently effected by treating the compound of formula B (either the respective α- or β-hydroxy isomers or mixtures thereof) with a mercapto substituted heterocycle corresponding to the desired SR substituent, in the presence of a small amount of a strong acid (e.g. typically about 0.01 to 0.1 moles per mole of the compound of formula B). Typically, this treatment is conducted at temperatures in the range of about from 0° to 50° C., (preferably about from 35° to 45° C.) for about from two to 24 hours, preferably about from six to eight hours using mole ratios of mercapto heterocycle to the compound of formula B of about from 1.0 to 5.0, preferably about from 1.1 to 1.5. Suitable inert organic solvents which can be used include, for example, tetrahydrofuran, dimethoxyethane, dioxane, chloroform, methylene chloride and the like. Suitable inert strong acids which can be used include, for example, perchloric acid, hydrochloric acid, hydrobromic acid, sulfuric acid, and the like. Suitable organic acids which can be used include, for example, p-toluenesulfonic acid, trifluoroacetic acid, and the like. Typically, superior results are obtained using p-toluenesulfonic acid.

Step 3, rearrangement of the cephem double bond and the orientation of the C-4-position ester group, can be conveniently effected by treating the compound of formula C with a catalytic amount of triethylamine in pyridine. Typically, this treatment is conducted under anhydrous conditions at temperatures in the range of about from 0° to 40° C., preferably about from 20° to 25° C. for about from 10 to 72 hours, preferably about from 24 to 36 hours using mole ratios of triethylamine to compound of formula C of about from 0.01 to 1.0, and preferably about from 0.05 to 0.1. Suitable organic solvents which can be used include, for example, pyridine, quinoline, N,N-dimethylaniline, and the like, and mixtures thereof. Also, in place of triethylamine, the following reagents could also be used, diisopropylethylamine, 1,5-diazabicyclo[5,4,0]undec-5-ene, 1,5-diazabicyclo-[4,3,0]-non-5-ene and the like. Alternatively, this rearrangement can be effected in two steps (3a and 3b) via the intermediate D. Step 3a can be conveniently effected by treating the compound of formula C in a suitable inert organic solvent. Typically, this treatment is conducted at temperatures in the range of about from −10° to 25° C., preferably about from 0° to 5° C. for about from 0.5 to 24 hours, preferably about from three to five hours, using mole ratios of m-chloroperbenzoic acid to compound of formula C of about from 1.0 to 1.2. Preferably this mole ratio should be close to one (about from 1.05 to 1.1) to prevent over oxidation of the thio moiety to sulfonyl). Suitable inert organic solvents which can be used include, for example, methylene chloride, chloroform, and the like, and mixtures thereof. Also, in place of m-chloroperbenzoic acid, the following reagents could also be used, perbenzoic acid, peracetic acid, hydrogen peroxide, sodium metaperiodate, ozone, and the like. Step 3b can be conveniently effected by treating the sulfoxide of formula D with a mixture of stannous chloride and acetyl chloride in a suitable inert organic solvent, preferably under an inert atmosphere. Typically, this treatment is conducted at temperatures in the range of about from −10° to 25° C., preferably from 0° to 5° C. for about from 0.25 to 5.0 hours, preferably about from 1.0 to 2.0 hours using mole ratios of stannous chloride to compound of formula D' of about from 1.5 to 5.0, and preferably about from 2.0 to 3.0. Also, in place of stannous chloride and acetyl chloride, the following reagents could also be used, phosphorous trichloride, phosphorous tribromide, and the like, and mixtures thereof.

Step 4 of the process can be conveniently effected by treating the compound of formula V' with phosphorus pentachloride in an inert organic solvent, in the presence of pyridine. This portion of step 4 is typically conducted under anhydrous conditions and under an inert atmosphere at temperatures in the range of about from 10° to 30° C. for about from 2.0 to 4.0 hours using 1.1 to 1.2 moles of pyridine and about from 1.1 to 1.2 moles of phosphorus pentachloride per mole of compound of formula V'. After the resulting reaction has been substantially completed, about from two to 10 moles of isobutyl alcohol, preferably about five, per mole of formula V' is added to the product mixture, and the treatment continued at temperatures in the range of about from −20° to 30° C., preferably about from 0° to 5° C. for about from 0.25 to 2.0 hours, preferably about from 0.5 to 1.0 hours. A small quantity of water is then added to effect the final reaction in this treatment. This final step is typically conducted at temperatures in the range of −20° to 30° C., preferably about from 0° to 5° C. for about from 0.1 to 1.0 hours, preferably about from 0.25 to 0.5 hours. Suitable inert organic solvents which can be used for this treatment include, for example, chloroform, and the like. Also, in place of pyridine, the following compounds could, for example, be used, quinoline, N,N-dimethylaniline, and the like. Also, in place of isbutyl alcohol, other lower alkanols could be used, for example, methanol, ethanol, and the like or mixtures thereof.

The next two steps of the process, i.e. acylation of the amino group and, if desired, removal of the ester group can be conducted interchangeably. Hence, the ester group can first be cleaved (step 7) and then the amino group acylated (step 8), or vice versa (i.e. steps 5 and 6). Step 7 or 6, any step 4a, can be effected by conventional procedures used by the art to cleave ester groups to yield the corresponding free acid, for example, benzhydryl and p-methoxybenzyl can be conveniently cleaved via treatment with a trifluoroacetic acid-anisole mixture (typically 2:1 to 6:1 mole ratio) at 0°–5° C. for about from two to five minutes in an inert solvent; e.g. methylene chloride, benzene, and the like.

Steps 5 and 8 can be effected by conventional amino acylation procedures. For example, steps 5 and 8 can be conveniently effected by treating the compounds of formulas II' and II'' with about from 1.1 to 1.5 stoichiometric equivalents of a suitable acyl halide, in an inert organic solvent (e.g. dichloromethane, chloroform, etc.) in the presence of an organic or inorganic base (e.g. sodium bicarbonate; pyridine; triethylamine and the like) at temperatures in the range of about from 0° to 5° C. for about from 0.5 to one hour. Typically, about from two to 10 stoichiometric equivalents of the base is used. The acylation can also be effected via treatment with a carboxy acid, having the desired $R^{1'}$ moiety (i.e. $R^{1'}$ COOH) and a suitable coupling reagent, e.g. dicyclohexyl carbodiimide or N-ethoxycarbonyl-2-ethoxy-1,2-dihydroquinoline, in a suitable inert organic solvent, e.g. dichloromethane. In the case of groups having an α-hydroxyacetyl or an α-free amino acetyl, it is preferred to use acyl halides, or $R^{1'}$ acids, in which the free hydroxy or free amino group is protected with a suitable protecting group which can be easily cleaved to yield the corresponding α-hydroxy or α-amino compounds. For example, the α-hydroxy compounds can be conveniently prepared via acylation with α-dichloroacetoxyphenacetyl halide to yield the corresponding α-dichloroacetyl protected free hydroxy derivative. The dichloroacetyl protecting group can then be removed via mild base hydrolysis. Similarly, the α-free amino compounds can be prepared via acylation with D-(−)-α-(t-butoxycarbonylamino)-α-phenylacetic acid to yield the corresponding t-butoxycarbonyl protected α-amino derivatives. The t-butoxycarbonyl protecting group can then be removed via acid hydrolysis. In either case, if the C-4 carboxy protecting group is also cleaved during the acid hydrolysis, it can be selectively replaced, if desired, via conventional procedures; for example, in the case of diphenylmethyl protecting groups via treatment with about a molar equivalent amount of diphenyldiazomethane.

The optical isomers of formulas III ($R^3$ is hydroxy, carboxy or sulfo) and IV can be conveniently prepared by using the corresponding optically active acyl halide or carboxy acid in the acylation step (step 5 or 8).

It is generally preferred that the respective products of each process step, described hereinabove, be separated and/or isolated prior to its use as starting material for subsequent steps. Separation and isolation can be effected by any suitable or purification procedure such as, for example, evaporation, crystallization, column chromatogrphy, thinlayer chromatography, distillation, etc. Specific illustrations of typical separation and isolation procedures can be had by reference to the appropriate examples described hereinbelow; however other equivalent separation procedures could, of course, also be used. Also, it should be appreciated that where typical reaction conditions (e.g. temperatures, mole ratios, reaction times) have been given that conditions both above and below these ranges can also be used, though generally less conveniently.

A second process for preparing the compounds of the invention can be schematically represented by the following sequence of overall reaction equations:

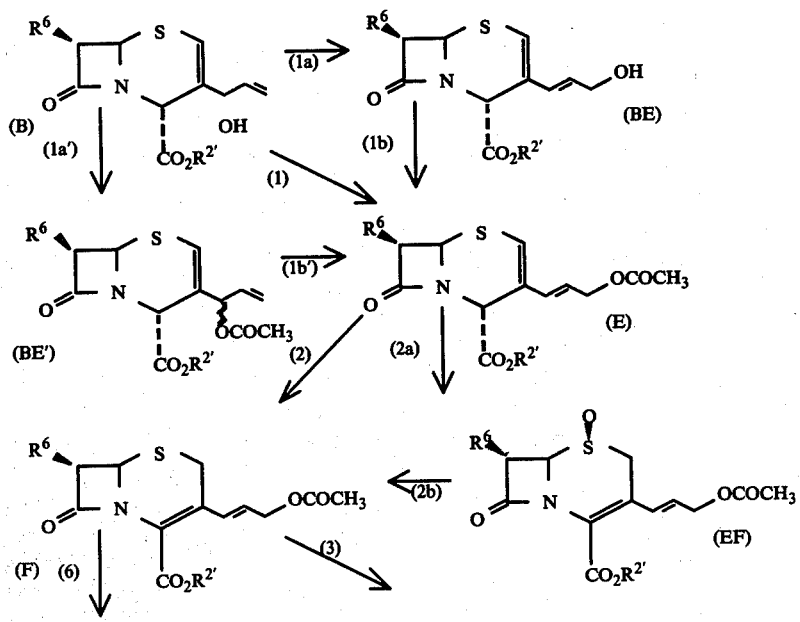

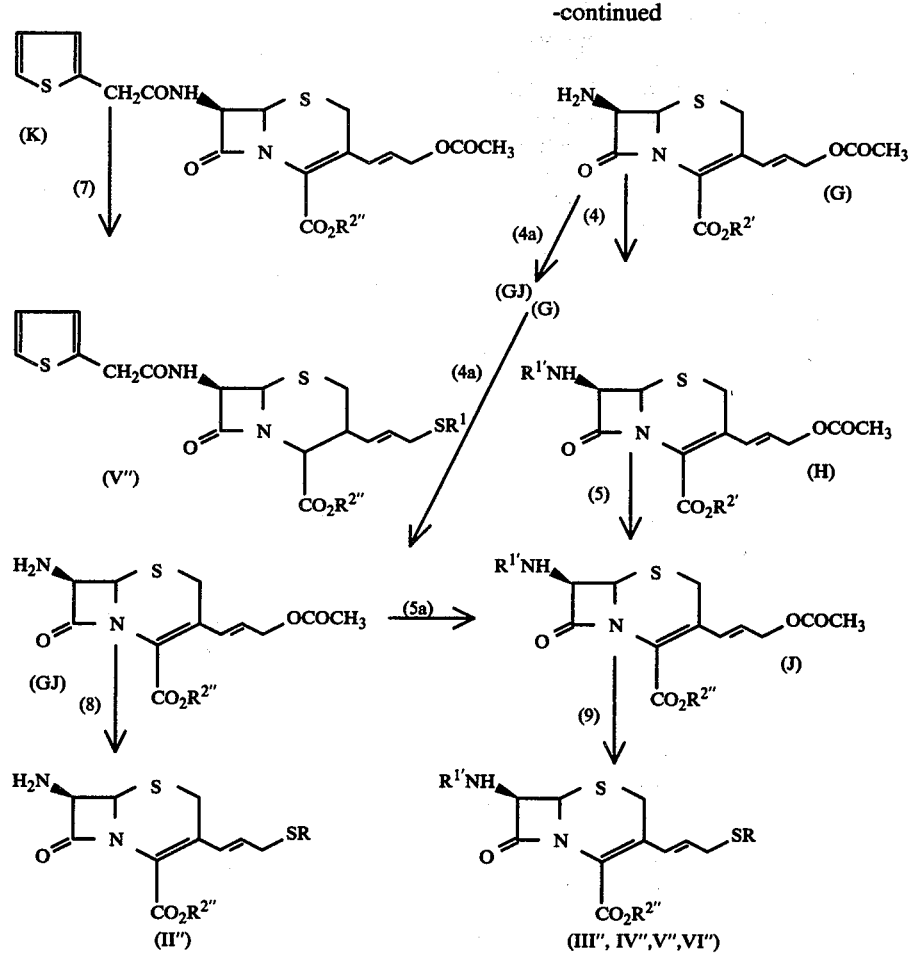

wherein R is as defined above; $R^{1'}$ is as defined above for $R^1$, but is other than hydrogen; $R^{2'}$ is a suitable protecting group, e.g. benzhydryl; $R^{2''}$ is hydrogen or a pharmaceutically acceptable cation, e.g. sodium; $R^6$ is the group

and the ~OH in formula B indicates a mixture of α- and β-hydroxy isomers.

Step 1, transformation of the 1-hydroxyprop-2-enyl group, directly to the 3-acetoxyprop-1-(t)-enyl group, can be effected in a single step by treatment of the starting material of formula B with acetic acid and p-toluenesulfonic acid in an inert organic solvent. Typically, this treatment is conducted at temperatures in the range of about from 0° to 70° C., preferably about from 30° to 40° C., for about from ½ to 12 hours, preferably about from four to eight hours, using mole ratios of acetic acid to starting material of formula B in the range of about from 5:1 to 500:1, preferably from about 20:1 to 40:1, and mole ratios of p-toluenesulfonic acid to starting material of formula B in the range of about from 1:1 to 1:100, preferably about from 1:10 to 1:20. Suitable inert organic solvents which can be used include, for example, tetrahydrofuran, dioxane, dimethoxyethane, dichloromethane, chloroform and the like and mixtures thereof. Also, in place of p-toluenesulfonic acid, the following acids could also be used: benzenesulfonic acid, perchloric acid, hydrochloric acid, sulfuric acid, and the like. Typically, best results are obtained using p-toluenesulfonic acid, and tetrahydrofuran as the inert organic solvent.

The starting material of formula B can be prepared according to the procedures described in the above identified parent applications and in Preparations 1-5 hereinbelow.

Alternatively, the rearrangement and esterification can be effected in two separate steps (i.e. steps 1a and 1b, respectively, or vice versa steps 1a' and 1b'). Step 1a can be effected by treating the material of formula B with p-toluenesulfonic acid, and water, in an inert organic solvent, such as tetrahydrofuran. Step 1b' can be effected by treating the material of formula BE' with p-toluenesulfonic acid, and acetic acid, in an inert organic solvent such as tetrahydrofuran. Typically, both rearrangements are conducted at temperatures in the range of about from 0° to 60° C., preferably about from 20° to 40° C., for about from one to 24 hours using mole ratios of p-toluenesulfonic acid to starting material of formula B or BE', in the range of about from 1:1 to 1:100, preferably from about 1:5 to 1:10, and mole ratios of water or acetic acid to compounds of formula B or BE' of about from 1:1 to 50:1. The same class of inert organic solvents and acids, which can be used in place of p-toluenesulfonic acid, as described hereinabove with respect to step 1, can also be used in this step.

Steps 1a' and 1b can be effected by treating the compound of formula B or BE with acetic acid or acetic anhydride in the presence of pyridine. Typically, this treatment is conducted at temperatures in the range of about from −20° to 50° C., preferably about from 0° to 5° C., for about from one to 24 hours, preferably four to eight hours using a mole ratio of acetic acid anhydride to compound of formula B or BE in the range of about from 1:1 to 50:1, preferably about from 10:1 to 20:1. The suitable inert organic solvents described hereinabove with respect to steps 1 and 1a can also be used in this step. Also, in place of pyridine, the following tertiary amines could also be used as catalysts for this step, quinoline, N,N-dimethylaniline, and the like.

Step 2, rearrangement of the cephem double bond can be conveniently effected by treating the compound of formula E with a catalytic amount of triethylamine in an inert organic solvent. Typically, this treatment is conducted under anhydrous conditions at temperatures in the range of about from −30° to 40° C., preferably about from −5° to 5° C. for about from 10 to 72 hours, preferably about from 24 to 36 hours using mole ratios of triethylamine to compound of formula E of about from 0.01 to 1, and preferably about from 0.05 to 0.1. Suitable inert organic solvents which can be used include, for example, pyridine, quinoline, N,N-dimethylaniline, and the like, and mixtures thereof. Typically, best results are obtained using pyridine. Also, in place of triethylamine, the following reagents could also be used, diisopropylethylamine, 1,6-diazabicyclo[5,4,0]undec-1-ene, 1,5-diazabicyclo[4,3,0] non-1-ene and the like. Alternatively, this rearrangement can be effected in two steps (2a and 2b) via the intermediate EF. Step 2a can be conveniently effected by treating the compound of formula E with m-chloroperbenzoic acid in a suitable inert organic solvent. Typically, this treatment is conducted at temperatures in the range of about from −10° to 25° C., preferably about from 0° to 5° C. for about from 0.5 to 24 hours, preferably about from three to five hours, using mole ratios of m-chloroperbenzoic acid to compound of formula E of about from 1.0 to 1.2. Preferably this mole ratio should be close to one (about from 1.05 to 1.1) to prevent over oxidation of the thio moiety to sulfonyl). Suitable inert organic solvents which can be used include, for example, methylene chloride (i.e. $CH_2Cl_2$), chloroform, and the like, and mixtures thereof. Also, in place of m-chloroperbenzoic acid, the following reagents could also be used, perbenzoic acid, peracetic acid, hydrogen peroxide, sodium metaperiodate, ozone, and the like. Step 2b can be conveniently effected by treating the sulfoxide of formula EF with a mixture of stannous chloride and acetyl chloride in a suitable inert organic solvent, preferably under an inert atmosphere; e.g. nitrogen. Typically, this treatment is conducted at temperatures in the range of about from −10° to 25° C., preferably from 0° to 5° C. for about from 0.25 to five hours, preferably about from ½ to two hours using mole ratios of stannous chloride to compound of formula EF of about from 1.5 to 5, and preferably about from 2 to 3. Also, in place of stannous chloride and acetyl chloride, the following reagents could also be used, phosphorous trichloride, phosphorous tribromide, and the like, and mixtures thereof.

Step 3 of the process can be conveniently effected by treating the compound of formula F with phosphorus pentachloride in an inert organic solvent, in the presence of pyridine. This portion of step 3 is typically conducted under anhydrous conditions and under an inert atmosphere (e.g. nitrogen) at temperatures in the range of about from 10° to 30° C. for about from two to four hours using 1.2 to 1.25 moles of pyridine and about from 1.1 to 1.2 moles of phosphorus pentachloride per mole of compound of formula F. After the resulting reaction has been substantially completed, about from one to 10 moles of isobutyl alcohol, preferably about from three to five moles, per mole of formula F is added to the product mixture, and the treatment continued at temperatures in the range of about from −20° to 30° C., preferably about from 0° to 5° C. for about from 0.25 to two hours, preferably about from 0.5 to one hour. A small quantity of water is then added to effect the final reaction in this treatment. This final step is typically conducted at temperatures in the range of −20° to 30° C., preferably about from 0° to 5° C. for about from 0.1 to one hour, preferably about from 0.25 to 0.5 hours, Suitable inert organic solvents which can be used for this treatment include, for example, methylene dichloride, chloroform, and the like. Also, in place of pyridine, the following compounds could, for example, be used, quinoline, N,N,-dimethylaniline, and the like. Also, in place of isobutyl alcohol, other lower alkanols could be used, for example, methanol, ethanol, and the like or mixtures thereof.

The next two steps of the process, i.e. acylation of the C-7 amino group and removal of the C-4 ester group and preparation of the C-4 carboxylate salt can be conducted interchangeably. Hence, the C-7 amino group can first be acylated (step 4) and then the C-4 ester group cleaved (step 5), or vice versa (i.e. steps 4a and 5a). Also, as should be apparent, compounds of formula K can be prepared by merely cleaving the C-4 protecting group from the compound of formula F (i.e. step 6).

Steps 4 and 5a can be effected by conventional amino acylation procedures. For example, steps 4 and 5a can be conveniently effected by treating the compound of formula G or GJ with about from 1.1 to 1.5 stoichiometric equivalents of a suitable acyl halide having the desired $R^1$ moiety, in an inert organic solvent (e.g. dichloromethane, chloroform, etc.) in the presence of an organic or inorganic base (e.g. sodium bicarbonate, pyridine, triethylamine and the like) at temperatures in the range of about from 0° to 5° C. for about from 0.5 to one hour. Typically, about from two to 10 stoichiometric equivalents of the base is used. The acylation can also be effected via treatment with a carboxy acid, having the desired $R^{1'}$ moiety (i.e. $R^{1'}COOH$) and a suitable coupling reagent, e.g. dicyclohexyl carbodiimide or N-ethoxycarbonyl-2-ethoxy-1,2-dihydroquinoline, in a suitable inert organic solvent, e.g. dichloromethane. In the case of groups having an α-hydroxyacetyl or an α-free amino-acetyl, it is preferred to use acyl halides, or $R^{1'}$ acids, in which the free hydroxy or free amino group is protected with a suitable protecting group, as described hereinbefore.

The optical isomers of formulas III (wherein $R^3$ is hydroxy or sulfo) and IV can be conveniently prepared by using the corresponding optically active acyl halide or carboxy acid in the acylation step (step 4 or 5a). In the case of the compounds of formula III wherein $R^3$ is carboxy, a reaction equilibrium exists between the respective D and L optical isomers and hence in this case the stable compound will exist as a mixture of the D and L isomers.

Steps 4a, 5 and 6 can be effected by conventional procedures used by the art to cleave ester groups to yield the corresponding free acid, for example, benzhydryl and p-methoxybenzyl can be conveniently cleaved via treatment with a neat trifluoroacetic acid-anisole mixture (typically 2:1 to 6:1 mole ratio) at about 0° to 5° C. for about from two to five minutes, or in an inert solvent; e.g. methylene chloride, benzene, and the like.

Steps 7, 8 and 9 can be effected by treating the desired compound of formula K, GJ or J with 5-mercapto-2-methyl-1,3,4-thiadiazole, 5-mercapto-3-methyl-1,2,4-thiadiazole or 5-mercapto-2-methyl-1,3,4-oxadiazole and an alkaline salt (e.g. sodium bicarbonate) in an aqueous solvent (preferably water). Typically this treatment is conducted at temperatures in the range of from 20° to 80° C., preferably about from 40° to 60° C., for about from two to 24 hours, preferably about from six to 10 hours using mole ratios of about 0.9 to 3, and preferably about from 1 to 1.2 moles of the desired 5-mercapto-heterocycle per mole of compound of formula K, GJ or J. Since best results are obtained by reacting the respective salts of formula K, GJ or H and the 5-mercapto compound, the purpose of the alkaline salt is to react with the free acid of formula K, GJ or H and the mercapto (H) to yield the corresponding salts. Hence, the mercapto salts of 5-mercapto-2-methyl-1,3,4-thiadiazole, 5-mercapto-3-methyl-1,2,4-thiadiazole and 5-mercapto-2-methyl-1,3,4-oxadiazole can be used in place of the free mercapto compounds and where the salts of both the compound of formula K, GJ or H and the mercapto reactant are used, the alkaline salt can be omitted. Typically, about from one to three mole equivalents of alkaline salt is used per mole of free acid of formula K, GJ or H and per mole of free mercapto compound. Suitable alkaline salts which can be used include, for example, sodium bicarbonate, potassium bicarbonate, sodium carbonate, potassium carbonate, and the like and mixtures thereof. Best results are obtained by using a mild alkaline salt such as, for example, sodium bicarbonate. Best results are obtained by using water as the solvent, however, aqueous mixtures of water and an inert organic solvent, e.g. methanol, ethanol, acetone, could also be used but typically afford no advantage. The initial product of this reaction is the corresponding salt of formula II'', III'', IV'', V'' or VI'' from which the free acid can be conveniently obtained by acidifying the reaction mixture (typically to pH 1 to 2). The desired pharmaceutically acceptable salt can then be prepared by treating the acid in the same manner as described hereinabove with respect to the compounds of the invention.

It is generally preferred that the respective product of each process step, described hereinabove, is separated and/or isolated prior to its use as starting material for subsequent steps. Separation and isolation can be effected by any suitable or purification procedure such as, for example, evaporation, crystallization, column chromatography, thin-layer chormatogrphy, distillation, etc. Specific illustrations of typical separation and isolation procedures can be had by reference to the appropriate examples described hereinbelow; however, other equivalent separation procedures could, of course, also be used. Also, it should be appreciated that where typical reaction conditions (e.g. temperatures, mole ratios, reaction times) have been given above that conditions both above and below these ranges can also be used, though generally less conveniently.

The pharmaceutically acceptable salts of the compounds of the invention can be prepared according to procedures which are well known in the art, for example, by simply treating the free acids of formulas III, IV, V and VI with an inorganic or organic base having the desired salt cation, e.g. sodium hydroxide, potassium hydroxide, triethylamine, ethanolamine, tris(hydroxymethyl)aminomethane, etc. The sodium salts can also be conveniently prepared by treating a solution of the acid in ethyl acetate with an excess of sodium-2-ethyl hexanoate. Compounds of formula III wherein $R^3$ is carboxy or sulfo are typically prepared as bis-salts.

The compounds of the invention, and salts thereof, have a broad spectrum of antibacterial activity against both gram positive and gram negative organisms such as *Stephylococcus aureus, Proteus vulgaris, Escherichia coli, Streptococcus pyogenes, Klebsiella pneumoniae,* and *Shigella sonnei.* The compounds can be used to combat or prophylactically to prevent infections of this nature in mammals and can be administered in the same manner as cephalothin or cephalosporin derivative drugs are generally administered (typically parenterally or orally). The compounds can be administered in a wide variety of dosage forms, either alone or in combination with other pharmaceutically compatible medicaments, in the form of pharmaceutical compositions suited for oral or parenteral administration. The dosage forms typically comprise the compounds (typically as pharmaceutically acceptable salts) and a pharmaceutical carrier and are preferably formulated in unit dosage form to facilitate the simple administration of precise dosages. The pharmaceutical carrier can be either a solid material or liquid, in which the compound is dissolved, dispersed or suspended. The dosage form can optionally contain other compatible medicaments, preservatives, emulsifying agents, wetting agents and/or pH-buffering agents. Suitable preservatives which can be used include, for example, benzyl alcohol and the like. Suitable buffering agents include, for example, sodium acetate and pharmaceutical phosphate salts and the like. Liquid dosage forms include, for example, solutions, suspensions, emulsions, syrups, elixirs, etc. Liquid carriers include, for example, water, saline solution, etc. Solid dosage forms include, for example, tablets, powders, capsules, pills, etc. Suitable solid carriers include, for example, pharmaceutical grades of starch, lactose, sodium saccharin, sodium bisulfite and the like.

The compounds of this invention are typically administered in dosages of about from 10 to 100 mg. per kg. per day of body weight. The precise effective dosage will, of course, vary depending upon the mode of administration, the condition being treated and the host.

The compounds can also be used as antiseptic agents in cleaning or disinfecting compositions, typically in solution form or suspended in a liquid carrier or in an aerosol spray.

Definitions

The following terms, as used hereinabove and below, have the following meaning unless expressly stated to the contrary. The term polyhaloalkyl refers to a halo substituted alkyl substituent having from one to six carbon atoms and containing at least two halogen atoms and includes both straight chain and branched polyhaloalkyl groups. The term halo or halide refers fluoro, chloro, bromo, or iodo or the corresponding halides. The term pharmaceutically acceptable salts refers to those salts of the parent compound which do not significantly adversely affect the pharmaceutical properties (e.g. toxicity, effectiveness, etc.) of the parent compound such as, for example, are conventionally used in the pharmaceutical art. The salts of the present invention are pharmaceutically acceptable cation salts, with respect to the acid and sulfo moieties and in case of formula II wherein $R^3$ is carboxy or sulfo can be prepared as both mono and bis salts. Suitable pharmaceutically acceptable cations include, for example, the alkali metals, e.g. sodium potassium, etc.; alkaline earth metals, e.g. calcium, etc.; ammonia; organic salts of triethylamine, diethylamine, tris(hydroxymethyl)aminomethane, ethanolamine, choline, caffeine and the like. The term 2-methyl-1,3,4-thiadiazol-5-yl- refers to the radical having the formula

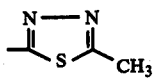

The term 3-methyl-1,2,4-thiadiazol-5-yl refers to the radical having the formula

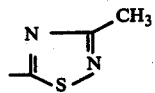

The term 2-methyl-1,3,4-oxadiazol-5-yl refers to the radical having the formula

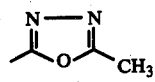

The term benzhydryl refers to the radical diphenylmethyl, i.e.

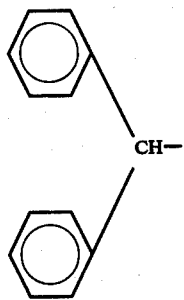

The term sydnon-3-yl refers to the radical having the formula

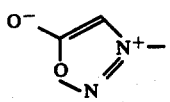

The term (1H)-tetrazol-1- yl refers to the radical having the formula

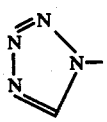

The term methoximino (fur-2-yl) acetamido refers to the syn(cis) isomeric form as regards the configuration of the methoxy group with respect to the carboxamido group. In this specification, the syn configuration is structurally denoted thus:

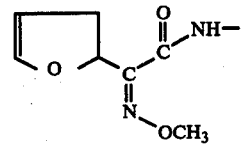

The term room temperature refers to about 20° Centigrade and all temperatures and temperature ranges refer to degrees centigrade. All percents refer to weight percents and the term equivalent mole amount refers to an amount stoichiometrically equivalent to the other reactant in the reaction referred to.

A further understanding of the invention can be had from the following non-limiting preparations and examples. Wherein proton magnetic resonance spectrum (n.m.r) are determined at 100 mHz (the signs of the coupling constants are not assigned) and signals are assigned as singlets (s), broad singlets (bs), doublets (d), double doublets (dd), triplets (t), double triplets (dt), quartets (q) and multiplets (m).

PREPARATION 1

3-Acetoxymethyl-7β-(thiophen-2-yl-acetamido)-ceph-2-em-4-carboxylic acid.

In this preparation 42 g. of cephalothin (i.e. 3-acetoxymethyl-7β-(thiophen-2-yl-acetamido)-ceph-3-em-4-carboxylic acid) is dissolved with warming in 130 ml. pyridine, and then cooled to about 18° C. 13 Ml. of acetic anhydride is added and the resulting mixture allowed to stand for two hours at room temperature affording a crystalline precipitate. Then 250 ml. of a 65:35, by vol., ethyl ether/ethyl acetate mixture is added and the resulting mixture stirred for one hour and then filtered. The recovered crystals are washed with 65 ml. of 65:35, by vol., ethyl acetate/ethyl ether solution and dried under vacuum to give 41 g. of the pyridinium salt of 3-acetoxymethyl-7β-(thiophen-2-yl-acetamido)-ceph-2-em-4-carboxylic acid. This salt is added to a mixture of 650 ml. water and 650 ml. ethyl acetate and the mixture then acidified to pH 2 using 20% aqueous hydrochloric acid. The ethyl acetate layer is separated and the aqueous layer further extracted with 400 ml. ethyl acetate. The combined ethyl acetate extracts are washed twice with brine, dried over anhydrous sodium sulfate and the solvent then removed under reduced pressure to afford 34 g. of 3-acetoxymethyl-7β-(thiophen-2-yl-acetamido)-ceph-2-em-4-carboxylic acid.

PREPARATION 2

3-Hydroxymethyl-7β-(thiophen-2-yl-acetamido)-ceph-2-em-4-carboxylic acid.

In this preparation 34 g. of 3-acetoxymethyl-7β-(thiophen-2-yl-acetamido)-ceph-2-em-4-carboxylic acid is added to a solution of 8.4 g. of lithium hydroxide monohydrate in 1000 ml. of water. The mixture is stirred at room temperature under nitrogen for two hours and then layered with 600 ml. of ethyl acetate. The pH of the mixture is then readjusted to pH 2 by the addition of 20% aqueous hydrochloric acid (~50 ml). The ethyl acetate layer is separated and the aqueous layer is extracted twice with 500 ml. portions of ethyl acetate. The combined ethyl acetate extracts are washed twice with brine, dried over anhydrous sodium sulfate and evaporated to dryness under reduced pressure affording 24.2 g. of 3-hydroxymethyl-7β-(thiophen-2-yl-acetamido)-ceph-2-em-4-carboxylic acid.

PREPARATION 3

Benzhydryl 3-hydroxymethyl-7β-(thiophen-2-yl-acetamido)-ceph-2-em-4-carboxylate.

In this preparation 24.2 g. of 3-hydroxymethyl-7β-(thiophen-2-yl-acetamido)-ceph-2-em-4-carboxylic acid is dissolved in 800 ml. of tetrahydrofuran, and then 15 g of diphenyldiazomethane is added to the solution and the resulting mixture stirred at room temperature for three hours. The mixture is evaporated to dryness under reduced pressure and 250 ml. of 90:10, vol., ethyl ether/methylene chloride solution is added to the residue. After the mixture is stirred for four hours, the solid is recovered by filtration, and washed with 100 ml. of 90:10 ethyl ether/methylene chloride and then dried affording 28.5 g. of benzhydryl 3-hydroxymethyl-7β-(thiophen-2-yl-acetamido)-ceph-2-em-4-carboxylate.

PREPARATION 4

Benzhydryl 3-formyl-7β-(thiophen-2-yl-acetamido)-ceph-2-em-4-carboxylate.

In this preparation 31. g. of dried chromium trioxide is added to a mixture of 51 g. of dry pyridine and 800 ml. of dry methylene chloride and stirred at 15° C. under nitrogen for 20 minutes. 26 Grams of benzhydryl 3-hydroxymethyl-7β-(thiophen-2-yl-acetamido)-ceph-2-em-4-carboxylate in 250 ml. of dry methylene chloride is added in one portion. The resulting mixture is stirred for 30 minutes and then filtered through diactomaceous earth. The contents of the reaction flask and the diatomaceous earth are washed with 500 ml. of methylene chloride and combined with the preceding filtrate and then washed with 400 ml. of 5% aqueous potassium hydroxide solution, 500 ml. of 20% aqueous hydrochloric acid and twice with 400 ml. brine. The aqueous washings are back extracted with 500 ml. of methylene chloride and the extracts added to the previously washed methylene chloride filtrate, then dried over sodium sulfate and then stirred for one hour with 30 g. of silica gel. The mixture is filtered and the silica gel washed with 400 ml. 1:1 vol. ethyl acetate/methylene chloride. The combined filtrates are evaporated to dryness under reduced pressure and the resulting residue (26 g.) is recyrstallized from ethyl ether/methylene chloride affording 21.4 g. of benzhydryl 3-formyl-7β-(thiophen-2-yl-acetamido)-ceph-2-em-4-carboxylate.

EXAMPLE 1

This example illustrates step 1 of the first process described for preparing the compounds of the invention. In this example 2.5 g. of benzhydryl 3-formyl-7β-(thiophen-2-yl-acetamido)ceph-2-em-4-carboxylate in 50 ml. of anhydrous tetrahydrofuran is stirred under nitrogen at −70° C. and 10 ml. of 2.5 molar solution of vinyl magnesium chloride is added dropwise over five minutes. After 15 minutes, 50 ml. of a pH 7 buffer solution of dibasic sodium phosphate and monobasic potassium phosphate is added to the well stirred mixture which is then warmed to room temperature. The mixture is diluted with 200 ml. of water and layered with 200 ml. of ethyl acetate. The pH of the aqueous layer is adjusted to pH 4 by the addition of 20% aqueous hydrochloric acid. The ethyl acetate layer is separated and the aqueous layer extracted with 100 ml. ethyl acetate. The ethyl acetate extracts are combined and then washed twice with 50 ml. portions of brine, dried over sodium sulfate and evaporated under reduced pressure affording benzhydryl 3-(1-hydroxyprop-2-enyl)-7β-(thiophen-2-yl-acetamido)-ceph-2-em-4-carboxylate as a pale yellow oil (2.7 g.).

The two isomers (α-hydroxy and β-hydroxy) are separated using thick-layer or column chromatrography on silica gel using 45:5 vol./vol. of methylene chloride/acetone. They are then characterized by their nmr spectra (both oils).

Isomer 1 (higher Rf), nmr (CDCl$_3$) δ:3.78 (s, 2H); 4.59 (bd, J 14Hz, 1H); 4.9–5.7 (m, 6H); 6.36 (s, 1H); 6.7–7.5 (m, 14H);

Isomer 2 (lower Rf), nmr (CDCl$_3$) δ:3.79 (s, 2H); 4.63 (m, 1H); 5.0–5.8 (m, 6H); 6.25 (s, 1H); 6.8–7.5 (m, 14H) ppm.

EXAMPLE 2

This example illustrates step 2 of the first process described for preparing the compounds of the invention. In this example, 2.7 g. of benzhydryl 3-(1-hydroxyprop-2-enyl)7β-(thiophen-2-yl-acetamido)-ceph-2-em-4-carboxylate is dissolved in 30 ml. tetrahydrofuran and stirred at 40° C., and 5-mercapto-2-methyl-1,3,4-thiadiazole (1.2 g.) and about 50 mg. of p-toluenesulfonic acid are added. The mixture is stirred for five hours at 40° C., then poured into 200 ml. of saturated aqueous sodium bicarbonate solution and extracted twice with 200 ml. portions of ethyl acetate. The ethyl acetate extracts are combined and washed with brine, dried over sodium sulfate and evaporated to dryness under reduced pressure affording 2.2 g. of an oil. This was chromatographed on 200 g. of silica gel eluting with 6:4 vol. ratio of ethyl acetate/hexane. The fractions which are homogeneous by thin-layer chromatography are combined affording 1.0 g. of benzhydryl 3-[3-(2-methyl-1,3,4-thiadiazol-5-ylthio)-prop-1-(t)-enyl]-7β-(thiophen-2-yl-acetamido)-ceph-2-em-4-carboxylate as an oil; nmr(CDCl$_3$)δ:2.67(3H,s); ~3.8(2H); 3.83(2H,s); 5.18(1H, d, J4Hz); 5.20(1H,s); 5.51(1H, dd, J4, 8Hz); 5.72(1H, dt, J15, 7Hz); 6.18 (1H, d, J15, Hz); 6.24 (1H, s); 6.59 (1H, d, J8Hz); 6.8–7.5(14H, m) ppm.

Similarly, benzhydryl 3-[3-(3-methyl-1,2,4-thiadiazol-5-ylthio)-prop-1-(t)-enyl]-7β-(thiophen-2-yl-acetamido)-ceph-2-em-4 carboxylate-oil; nmr (CDCl$_3$)δ:2.54(3H,s); 3.72(2H,d, J7Hz); 3.80(2H,s); 5.20(1H,d,J4Hz); 5.22(1H,s); 5.51(1H, dd, J4, 8Hz); 5.70(1H, dt, J15.5, 7Hz); 6.19(1H, d, J15.5Hz); 6.28(1H,s); 6.64(1H, d, J8Hz); 6.8–7.5 (14H, m) ppm and benzyhydryl 3-[3-(2-methyl-1,3,4-oxadiazol-5-ylthio)-prop-(t)-enyl[-7β-(thiophen-2-yl-acetamido)-ceph-2-em-4-carboxylateoil; nmr (CDCl$_3$)δ:2.44 (3H, s); 3.7(2H, m); 3.82(2H,s); 5.20 (2H, 6s); 5.52(1H, dd, J4, 8Hz); 5.69(1H, dt, J16, 7Hz); 6.20 (1H, d, J16Hz); 6.27(1H, s); 6.55(1H, d, J8Hz); 6.87-7.5 (14H, m)ppm are prepared by following the same procedure but using 5-mercapto-3-methyl-1,2,4-thiadiazole and 5-mercapto-2-methyl-1,3,4-oxadiazole in place of 5-mercapto-2-methyl-1,3,4-thiadiazole.

EXAMPLE 3

This example illustrates step 3 of the first process described for preparing the compounds of the invention. In this example, a solution of 1.4 g. of benzhydryl 3-[3-(2-methyl-1,3,4-thiadiazol-5-ylthio)-prop-1-(t)-enyl]-7β-(thiophen-2-yl-acetamido)-ceph-2-em-4-carboxylate in 10 ml. of dry pyridine is treated with 0.1 ml. of triethylamine. The mixture is allowed to stand at room temperature for 20 hours and then evaporated to dryness under reduced pressure. The resulting residue is chromatographed on 100 g. of silica gel eluting with 15% vol. ethyl acetate/benzene affording 370 mg. of benzhydryl 3-[3-(2-methyl-1,3,4-thiadiazol-5-ylthio)-prop-1-(t)-enyl]-7β-(thiophen-2-yl-acetamido)-ceph-3-em-4-carboxylate and 650 mg. of the starting material i.e., benzhydryl 3-[3-(2-methyl-1,3,4-thiadiazol)-prop-1-(t)-enyl]-7β-(thiophen-2-yl-acetamido)-ceph-2-em-4-carboxylate. The recovered starting material is treated in the same manner as above, affording another 200 mg. of benzhydryl 3-[3-(2methyl-1,3,4-thiadiazol-5-ylthio-prop-1-(t)-enyl]-7β-(thiophen-2-yl-acetamido)-ceph-3-em-4-carboxylate; m.p. 172°–173° C.; $[\alpha]_D -161°$ (CHCl$_3$); uv (EtOH):306nm ($\epsilon$20,200); ir(KBr) : 1775, 1725, 1660cm$^{-1}$; nmr (CDCl$_3$)δ2.67(3H,s); 3.44(2H,bs); 3.81(2H,s); 3.84(2H,d,J7Hz); 4.97(1H,d,J4Hz); 5.81(1H,dd,J4,8Hz); 6.09(1H,dt,J 15.5,7Hz); 6.48(1H,d,J8Hz); 6.90(1H,d,J 15.5Hz); 6.9–7.5(14H,m)ppm; Anal. Found: C, 58.53; H, 4.29; N, 8.24%. C$_{32}$H$_{28}$N$_4$O$_4$S$_4$ requires C, 58.16,H, 4.27,N, 8.49%.

Similarly, benzhydryl 3-[3-(3-methyl-1,2,4-thiadiazol-5-ylthio)-prop-1-(t)-enyl]-7β-(thiophen-2-yl-acetamido)-ceph-3-em-4-carboxylate [m.p. 149°–150° C.; $[\alpha]_D$-144°(CHCl$_3$); uv(EtOH) 306 nm($\epsilon$ 20,600); ir(KBr) 1785,1730,1660cm$^{-1}$; nmr(CDCl$_3$)δ:2.57 (3H,s); 3.45(2H,bs); 3.83(2H,s); 3.85(2H,d,J7Hz)4.96(1H,d,J4.5 Hz); 5.81(1H,dd,J4.5,9Hz); 5.95(1H,dt,J15.5,7Hz); 6.54(1H,d, J9Hz); 6.8–7.5(15H,m)ppm. Anal. Found: C,58.45,H,4.07,N,8.45%. [C$_{32}$H$_{28}$, N$_4$O$_4$S$_4$ requires C,58.16,H,4.27,N8.49%] and benzhydryl 3-[3-(2-methyl-1,3,4-oxadiazol-5-ylthio)-prop-1-(t)-enyl]-7β-(thiophen-2-yl-acetamido)-ceph-3-em-4-carboxylate[m.p.158°–160° C.; $[\alpha]_D$-153° (CHCl$_3$); uv(EtOH)304nm($\epsilon$ 20,000); ir(KBr)1775,1725, 1665cm$^{-1}$; nmr(CDCl$_3$)δ:2.43(3H,s); 3.43(2H,bs); 3.76(2H,d,J7Hz); 3.81(2H,s); 4.95(1H,d,J4.5Hz); 5.80(1H,dd,J4.5,9Hz); 6.05(1H,dt,J16,7Hz); 6.52(1H,d,J9Hz); 6.8–7.5(15H,m)ppm; Anal Found: C,59.61; H,4.36; N,8.40%. [C$_{32}$H$_{28}$N$_4$O$_5$S$_3$ requires C, 59.61; H,4.38; N,8.69%] are prepared by the following the same procedure but using benzhydryl 3-[3-(3-methyl-1,2,4-thiadiazol-5-ylthio)-prop-1-(t)-enyl]-7β-(thiophen-2-yl-acetamido)-ceph-2-em-4-carboxylate and 3-[3-(2-methyl-1,3,4-oxadiazol-5-ylthio)-prop-1-(t)-enyl]-7β-(thiophen-2-yl-acetamido)-ceph-2-em-4-carboxylate in place of benzhydryl 3-[3-(2-methyl-1,3,4-thiadiazol-5-ylthio)-prop-1-(t)-enyl]-7β-(thiophen-2-yl-acetamido)-ceph-2-em-carboxylate.

EXAMPLE 3A

This example illustrates step 3a of the first process described for preparing the compounds of the invention. In this example, 2.2 g. of benzhydryl 3-[3-(2-methyl-1,3,4-thiadiazol-5-ylthio)-prop-1-(t)-enyl]-7β-(thiophen-2-yl-acetamido)-ceph-2-em-4-carboxylate in 50 ml. of methylene chloride is stirred at 25° and 85% m-chloroperbenzoic acid (0.72g.) is added in portions over two hours. The mixture is further diluted with methylene chloride and washed with excess dilute aqueous sodium bicarbonate solution, dried over anhydrous sodium sulfate and evaporated under reduced pressure to give a yellow foam. This is chromatographed on silica gel, eluting with acetone/methylene chloride 15:85 vol. The pure fractions are combined affording 1.1 g. of benzhydryl 3-[3-(2-methyl-1,3,4-thiadiazol-5-ylthio-prop-1-(t)-enyl]-7β-thiophen-2-yl-acetamido)-ceph-3-em-4-carboxylate-1-oxide as a white crystalline solid.

Similarly, benzhydryl 3-[3-(3-methyl-1,2,4-thiadiazol-5-ylthio)-prop-1-(t)-enyl]-7β-(thiophen-2-yl-acetamido)-ceph-3-em-4-carboxylate-1-oxide and 3-[3-(2-methyl-1,3,4-oxadiazol-5-ylthio)-prop-1-(t)-enyl]-7β-(thiophen-2-yl-acetamido)-ceph-3-em-4-carboxylate-1-oxide are prepared by following the same procedure using 3-[3-(3-methyl-1,2,4-thiadiazol-5-ylthio)-prop-1-(t)-enyl]-7β-(thiophen-2-yl-acetamido)-ceph-2-em-4-carboxylate and 3-[3-(2-methyl-1,3,4-oxadiazol-5-ylthio)-prop-1-(t)-enyl]-7β-(thiophen-2-yl-acetamido)-ceph-2-em-4-carboxylate as starting materials.

EXAMPLE 3B

This example illustrates step 3b of the first process described for preparing the compounds of the invention. In this example, 1.0 g. of benzhydryl 3-[3-(2-methyl-1,3,4-thiadiazol-5-ylthio)-prop-1-(t)-enyl]-7β-(thiophen-2-yl-acetamido)-ceph-3-em-4-carboxylate-1-oxide is dissolved in 10 ml. of dry dimethylformamide and the solution stirred at 0° C. under nitrogen while stannous chloride (1.0 g.) and acetyl chloride (2 ml.) are added with stirring. Stirring is continued while the solution is warmed to room temperature and continued for another 20 minutes. The mixture is then diluted with water and extracted twice with ethyl acetate. The combined extracts are washed twice with water and brine, dried over sodium sulfate and evaporated under reduced pressure affording 0.8 g. of a yellow oil. This is chromatographed on silica gel eluting with acetone/methylene chloride (5:95 vol.) yielding 200m.g. g. of benzhydryl 3-[3-(2-methyl-1,3,4-thiadiazol-5-ylthio)-prop-1-(t)-enyl]-7β-(thiophen-2-yl-acetamido)-ceph-3-em-4-carboxylate as a white crystalline solid.

Similarly, benzhydryl 3-[3-(3-methyl-1,2,4-thiadiazol-5-ylthio)-prop-1-(t)-enyl]-7β-(thiophen-2-yl-acetamido)-ceph-3-em-4-carboxylate and benzhydryl 3-[3-(2-methyl-1,3,4-oxadiazol-5-ylthio)-ceph-3-em-4-carboxylate are prepared using 3-[3-(3-methyl-1,2,4-thiadiazol-5-ylthio)-1-(t)-enyl]-7β-(thiophen-2-yl-acetamido)-ceph-3-em-4-carboxylate-1-oxide and 3-[3-(2-methyl-1,3,4-oxadiazol-5-ylthio)-prop-1-(t)-enyl]-7β-(thiophen-2-yl-acetamido)-ceph-3-em-4-carboxylate-1-oxide as starting materials.

EXAMPLE 4

This example illustrates step 4 of the first process described for preparing the compunds of the invention. In this example, 0.21 g. of benzhydryl 3-[3-(2-methyl-1,3,4-thiadiazol-5-ylthio)-prop-1-(t)-enyl]-7β-(thiophen-2-yl-acetamido)-ceph-3-em-4-carboxylate is stirred at room temperature under nitrogen in 10 ml. of dry methylene chloride and 28 μl. of pyridine. Phosphorous pentachloride (73 mg.) is then added. The mixture is stirred for two hours at room temperature, then cooled to 0° C. and 0.2 ml. of isobutyl alcohol is added and stirring continued for 40 minutes. Then 0.5 ml. of water is added and the mixture is stirred vigorously for 15 minutes. The mixture is then diluted with excess dilute aqueous sodium bicarbonate solution and extracted twice with ethyl acetate. The combined extracts are washed with water and brine, dried over sodium sulfate, and evaporated under reduced pressure affording benzhydryl 3-[3-(2-methyl-1,3,4-thiadiazol-5-ylthio)-prop-1-(t)-enyl]-7β-amino-ceph-3-em-4-carboxylate.

Similarly, benzhydryl 3-[3-(3-methyl-1,2,4-thiadiazol-5-ylthio)-prop-1-(t)-enyl]-7β-aminoceph-3-em-4-carboxylate and benzhydryl 3-[3-(2-methyl-1,3,4-oxadiazol-5-ylthio)-prop-1-(t)-enyl]-7β-amino-ceph-3-em-4-carboxylate are prepared by following the same procedure using benzhydryl 3-[3-(3-methyl-1,2,4-thiadiazol-5-ylthio)-prop-1-(t)-enyl]-7β-(thiophen-2-yl-acetamido)-ceph-3-em-4-carboxylate and benzhydryl 3-[3-(2-methyl-1,3,4-oxadiazol-5-ylthio)-prop-1-(t)-enyl]-7β-(thiophen-2-yl-acetamido)-ceph-3-em-4-carboxylate as starting materials.

EXAMPLE 4A

This example illustrates step 4a of the first process described for preparing the compounds of the invention. In this example, 42mg. of benzhydryl 3-[3-(2-methyl-1,3,4-thiadiazol-5-ylthio)-prop-1-(t)-enyl]-7β-(thiophen-2-ylacetamido)-ceph-3-em-4-carboxylate ester and 0.5 ml. of anisole are stirred together at 0° C. and 2.5 ml. of trifluoroacetic acid is then added. The mixture is stirred vigorously for two minutes and then rapidly evaporated to dryness under reduced pressure. The resulting crude 3-[3-(2-methyl-1,3,4-thiadiazol-5-ylthio)-prop-1-(t)-enyl]-7β-(thiophen-2-ylacetamido)-ceph-3-em-4-carboxylic acid is dissolved in tetrahydrofuran and then filtered. The resulting filtrate is treated with an excess of a solution of sodium 2-ethylhexanoate in tetrahydrofuran and then evaporated to dryness. The residue is mixed with isopropanol and stirred at room temperature for one hour. The resulting solid is collected by filtration, washed three times with isopropanol and dried under vacuum affording 25 mg. of sodium 3-[3-(2-methyl-1,3,4-thiadiazol-5-ylthio)-prop-1-(t)-enyl]-7β-(thiophen-2-ylacetamido)-ceph-3-em-4-carboxylate;mp. 200° C. (decomp); UV($H_2O$): 297nm ($\epsilon$ 22,000); ir(KBr): 1760, 1655, 1605 $cm^{-1}$; nmr(DMSO-$d_6$) δ:2.64(3H,s); 3.44(2H,s); 3.74(2H,s); 3.95(2H,d,J7Hz); 4.99(1H,d,J4Hz); 5.49(1H,dd, J4,8Hz); 5.74(1H,dt,J16,7Hz); 6.8–7.0(2H,m); 7.10(1H,d,J16Hz); 7.2–7.4(1H,m); 9.05(1H,d,J8Hz) ppm.

Similarly, the sodium salt of 3-[3-(3-methyl-1,2,4-thiadiazol-5-ylthio)-prop-1-(t)-enyl]-7β-(thiophen-2-ylacetamido)-ceph-3-em-4-carboxylic acid which decomposes before melting [uv($H_2O$): 297nm($\epsilon$ 21,500); ir(KBr): 1755, 1660, 1615 $cm^{-1}$; nmr(DMSO-$d_6$)δ:2.50(3H,s); 3.46(2H,bs); 3.76(2H,s); 4.00(2H,d,J8Hz); 4.98(1H,d,J4.5Hz); 5.48(1H,dd,J4.5,8Hz); 5.70(1H,dt,J16,8Hz); 6.80–7.0(2H,m); 7.24(1H,d,J16Hz); 7.2–7.4(1H,m); 9.08(1H,d,J8Hz)ppm] and the sodium salt of 3-[3-(2-methyl-1,3,4-oxadiazol-5-ylthio)-prop-1-(t)-enyl]-7β-(thiophen-2-ylacetamido)-ceph-3-em-4-carboxylic acid which also decomposes before melting [uv($H_2O$): 298nm ($\epsilon$ 21,000); ir(KBr): 1760, 1665, 1615 $cm^{-1}$; nmr(DMSO-$d_6$) δ:2.50(3H,s); 3.42(2H,bs); 3.76(2H,s); 3.92(2H,d,J7Hz); 4.99(1H,d,J4.5Hz); 5.49(1H,dd,J4.5,8Hz); 5.70(1H,dt,J15,7Hz); 6.8–7.0(2H,m); 7.10(1H,d,J15Hz); 7.2–7.4(1H,m); 9.07(1H,d,J8Hz)ppm] are prepared by following the same procedure using benzhydryl 3-[3-(3-methyl-1,2,4-thiadiazol-5-ylthio)-prop-1-(t)-enyl]-7β-(thiophen-2-ylacetamido)-ceph-3-em-4-carboxylate and benzhydryl 3-[3-(2-methyl-1,3,4-oxadiazol-5-ylthio)-prop-1-(t)-enyl]-7β-(thiophen-2-ylacetamido)-ceph-3-em-4-carboxylate as starting materials.

EXAMPLE 5

This example illustrates steps 5 and 6 of the first process described for preparing the compounds of the invention. In this example, 0.1 ml. of D-α-dichloroacetoxyphenylacetyl chloride is added to a stirred mixture of 120mg. of benzhydryl 3-[3-(3-methyl-1,2,4-thiadiazol-5-ylthio)-prop-1-(t)-enyl]-7β-amino-ceph-3-em-4-carboxylate and 0.5ml. of pyridine in 10 ml. of methylene chloride. After stirring for 15 minutes at room temperature, the mixture is washed with dilute hydrochloric acid, then with dilute aqueous sodium bicarbonate and then dried over sodium sulfate and evaporated to give a brown oil. The oil is purified using thick-layer chromatography on silica gel eluting with methylene chloride/acetone, 19:1, affording 55mg. of benzhydryl 3-[3-(3-methyl-1,2,4-thiadiazol-5-ylthio)-prop-1-(t)-enyl]-7β-D-(α-hydroxy-α-phenylacetamido)-ceph-3-em-4-carboxylate.

The above obtained ester is treated with 0.5ml. anisole and 2.5ml. trifluoroacetic acid at 0° C. After 3 minutes the mixture is concentrated to dryness under reduced pressure and the resulting residue is taken up in ethyl acetate. The ethyl acetate solution is then extracted with saturated aqueous sodium bicarbonate. The extract is allowed to stand at room temperature for 2 hours and is then rendered acidic with dilute hydrochloric acid extracted twice with ethyl acetate. The combined extracts are washed with brine, dried over sodium sulfate and evaporated to afford a residue of crude 3-[3-(3-methyl-1,2,4-thiadiazol-5-ylthio)-prop-1-(t)-enyl]-7β-D-(60-hydroxy-α-phenylacetamido)-ceph-3-em-4-carboxylic acid.

The above obtained acid is dissolved in ethyl acetate and the sodium salt precipitated by the addition of 0.1 g. of sodium 2-ethylhexanoate. The sodium salt is collected by filtration, washed twice with ethyl acetate and dried under vacuum affording 25mg. of sodium 3-[3-(3-methyl-1,2,4-thiadiazol-5-ylthio)-prop-1-(t)-enyl]-7β-D-(α-hydroxy-α-phenylacetamido)-ceph-3-em-4-carboxylate as a white powder which decomposes on melting; uv($H_2O$):296nm($\epsilon$ 20,900); ir(KBr)1760, 1660, 1610 $cm^{-1}$; nmr(DMSO-$d_6$) δ:250(3H,s); 3.40(2H,bs); 3.99(2H,d,J7.5Hz); 4.98(1H,d,J5Hz); 5.10(1H,s); 5.5(1H,m); 5.7(1H,m); 7.0–7.5 (6H,m); 8.51(1H,d,J8Hz)ppm.

Similarly, the sodium salts of 3-[3-(2-methyl-1,3,4-thiadiazol-5-ylthio)-7β-D-(α-hydroxy-α-phenylacetamido)-ceph-3-em-4-carboxylic acid and 3-[3-(2-methyl-1,3,4-oxadiazol-5-ylthio)-prop-1-(t)-enyl]-7α-D-(α-hydroxy-α-phenylacetamido)-ceph-3-em-4-carboxylic acid are prepared by following the same procedure using benzhydryl 3-[3-(2-methyl-1,3,4-thiadiazol-5-ylthio)]-7β-amino-ceph-3-em-4-carboxylate and benzhydryl 3-[3-(2-methyl-1,3,4-oxadiazol-5-ylthio)-prop-1-(t)-enyl]-7β-amino-ceph-3-em-4-carboxylate as starting materials.

EXAMPLE 6

This example illustrates steps 5 and 6 of the first process described for preparing the compounds of the invention. In this example, 0.1 g. of α-(t-butoxycarbonyl)-α-phenylacetic and 0.15 g. of dicyclohexylcarbodiimide are added to a mixture of 0.12 g. of benzhydryl 3-[3-(2-methyl-1,3,4-thiadiazol-5-ylthio)-prop-1-(t)-enyl]-7β-amino-ceph-3-em-4-carboxylate in 10 ml. of dichloromethane. The reaction mixture is then stirred at room temperature for four hours and then 2 ml. of a saturated solution of oxalic acid in methanol is added. After ten minutes the mixture is filtered and the filtrate recovered and diluted with ethyl acetate, then washed with aqueous sodium bicarbonate solution, then brine, and then dried over sodium sulfate and evaporated to dryness under reduced pressure to afford a residue of crude 3-[3-(2-methyl-1,3,4-thiadiazol-5-ylthio)-prop-1-(t)-enyl]-7β-(α-t-butoxycarbonyl-α-phenylacetamido)-ceph-3-em-4-carboxylate.

Trifluoroacetic acid (2.5ml) is then added to a stirred mixture of 0.1 g. of the above obtained ester and 0.5 ml. of anisole at 0° C. Vigorous stirring is maintained at this temperature for 30 minutes. The mixture is then evaporated to dryness under reduced pressure and the residue is washed twice with ethyl ether and then dissolved in ethyl acetate, and then filtered affording a filtrate containing 3-[3-(2-methyl-1,3,4-thiadiazol-5-ylthio)-prop-1-(t)-enyl]-7β-(α-carboxy-α-phenylacetamido)-ceph-3-em-4-carboxylic acid. The filtrate is then treated with an excess of sodium 2-ethylhexanoate in ethyl acetate and then evaporated to dryness under reduced pressure. The residue is stirred with 5 ml. of isopropanol for one hour and then filtered. The recovered residue is washed twice with isopropanol, once with ethyl acetate and then dried under vacuum to afford 3-[3-(2-methyl-1,3,4-thiadiazol-5-ylthio)-prop-1-(t)-enyl]-7β-(α-carboxy-α-phenylacetamido)-ceph-3-em-4-carboxylic acid disodium salt.

Similarly, the disodium salts of 3-[3-(3-methyl-1,2,4-thiadiazol-5-ylthio)-prop-1-(t)-enyl]-7β-(α-carboxy-α-phenylacetamido)-ceph-3-em-4-carboxylic acid and 3-[3-(2-methyl-1,3,4-oxadiazol-5-ylthio)-prop-1-(t)-enyl]-7β-(α-carboxy-α-phenylacetamido)-ceph-3-em-4-carboxylic acid are prepared by following the same procedure using benzhydryl 3-[3-(3-methyl-1,2,4-thiadiazol-5-ylthio)-prop-1-(t)-enyl]-7β-amino-ceph-3-em-4-carboxylate and 3-[3-(2-methyl-1,3,4-oxadiazol-5-ylthio)-prop-1-(t)-enyl]-7β-amino-ceph-3-em-4-carboxylate as starting materials.

EXAMPLE 7

This example illustrates steps 5 and 6 of the first process described for preparing the compounds of the invention. In this example, a mixture containing 0.5g. of benzhydryl 3-[3-(2-methyl-1,3,4-thiadiazol-5-ylthio)-prop-1-(t)-enyl]-7β-amino-ceph-3-em-4-carboxylate, 0.4 g. of D-(−)-α-(t-butoxycarbonylamino)-α-phenylacetic acid and 0.5 g. of dicyclohexylcarbodiimide in 25 ml. of dichloromethane is stirred at room temperature for two hours and then 2 ml. of a saturated solution of oxalic acid in methanol is added. After ten minutes, the mixture is filtered. The filtrate is diluted with ethyl acetate, washed successively with sodium bicarbonate solution and brine, dried over sodium sulfate and then evaporated to dryness to afford benzhydryl 3-[3-(2-methyl-1,3,4-thiadiazol-5-ylthio)-prop-1-(t)-enyl]-7β-[α-t-butoxycarbonylamino)-α-phenylacetamido]-ceph-3-em-4-carboxylate.

Trifluroacetic acid (3 ml) is added to a stirred mixture of 0.17 g. of the above obtained ester and 0.5 ml. of anisole at 0° C. The mixture is stirred vigorously for 30 minutes at 0° C. and then evaporated to dryness under reduced pressure. The residue is mixed with ethyl ether, filtered and the trifluoroacetic acid salt of 3-[3-(2-methyl-1,3,4-thiadiazol-5-ylthio)-prop-1-(t)-enyl]-7β-D-(α-amino-α-phenylacetamido-ceph-3-em-4-carboxylic acid is collected. This salt is then stirred with a mixture of 0.5 ml. of water and 0.5 ml. of 25%, wt., suspension of a water immiscible polymeric amine, sold under the Trademark Amberlite LA-1, by Rohm & Haas Company of Philadelphia, Pa., in methylisobutyl ketone, for one hour; the resulting solid is collected by filtration, then washed with 1:1 vol. water:methyl isobutyl ketone, then methyl isobutyl ketone, then ethyl acetate, and then dried under vacuum affording 3-[3-(2-methyl-1,3,4-thiadiazol-5-ylthio)-prop-1-(t)-enyl]-7β-D-(α-amino-α-phenylacetamido-ceph-3-em-4-carboxylic acid.

Similarly, 3-[3-(3-methyl-1,2,4-thiadiazol-5-ylthio)-prop-1-(t)-enyl]-7β-D-(α-amino-α-phenylacetamido)-ceph-3-em-4-carboxylic acid and 3-[3-(2-methyl-1,3,4-oxadiazol-5-ylthio)-prop-1-(t)-enyl]-7β-D-(α-amino-α-phenylacetamido)-ceph-3-em-4-carboxylic acid are prepared by following the same procedure using benzhydryl 3-[3-(3-methyl-1,2,4-thiadiazol-5-ylthio)-prop-1-(t)-enyl]-7β-amino-ceph-3-em-4-carboxylate and benzhydryl 3-[3-(2-methyl-1,3,4-thiadiazol-5-ylthio)-prop-1-(t)-enyl]-7β-amino-ceph-3-em-4-carboxylate as starting materials.

In like manner, by replacing D-(−)-α-(t-butoxycarbonylamino)-α-phenylacetic acid with D-(−)-α-(t-butoxycarbonylamino)-α-(p-hydroxyphenyl) acetic acid, the following compounds are prepared:

3-[3-(2-methyl-1,3,4-thiadiazol-5-ylthio)-prop-1-(t)-enyl]-7β-D-[α-amino-α(p-hydroxyphenyl)acetamido]-ceph-3-em-4-carboxylic acid;

3-[3-(3-methyl-1,2,4-thiadiazol-5-ylthio)-prop-1-(t)-enyl]-7β-D-[α-amino-α(p-hydroxyphenyl)acetamido]-ceph-3-em-4-carboxylic acid; and 3-[3-(2-methyl-1,3,4-oxadiazol-5-ylthio)-prop-1-(t)-enyl]-7β-D-[α-amino-α-(p-hydroxyphenyl)acetamido]-ceph-3-em-4-carboxylic acid.

EXAMPLE 8

This example illustrates steps 5 and 6 of the first process described for preparing the compounds of the invention. In this example, a mixture of 0.09 g. of benzhydryl 3-[3-(2-methyl-1,3,4-thiadiazol-5-ylthio)-prop-1-(t)-enyl]-7β-amino-ceph-3-em-4-carboxylate and 1 ml. of pyridine, in 13 ml. of chloroform is stirred at room temperature and 0.08 g. of 1H-tetrazol-1-ylacetyl chloride, in 1 ml. of chloroform, is added. The mixture is stirred for 30 minutes, then diluted further with chloroform, washed with dilute aqueous hydrochloric acid and brine, dried over anhydrous sodium sulfate, and then evaporated under reduced pressure yielding an oily residue. The residue is purified using thick layer chromatography on silica gel eluting with acetone-dichloromethane, 1:4, affording benzhydryl 3-[3-(2-methyl-1,3,4-thiadiazol-5-ylthio)-prop-1-(t)-enyl]-7β-[α-(1H)-tetrazol-1-ylacetamido]-ceph-3-em-4-carboxylate.

A mixture of 0.035g. of the above obtained ester and 0.5 ml. of anisole is stirred at 0° C. and 2.5ml. of trifluoroacetic acid is then added. The mixture is stirred vigorously for two minutes, then rapidly evaporated to dryness under reduced pressure. The resulting crude 3-[3-(2-methyl-1,3,4-thiadiazol-5-ylthio)-prop-1-(t)-enyl]-7β-(α-1H-tetrazol-1-ylacetamido)-ceph-3-em-4-carboxylic acid is treated then with ethyl ester. The solid which separates is collected by filtration and then dissolved in tetrahydrofurn and filtered, and the filtrate treated with an excess of a solution of sodium 2-ethylhexanoate in tetrahydrofuran. The mixture is evaporated to dryness and the resulting residue mixed with isopropanol. The solid which separates is collected by filtration, washed three times with isopropanol and dried under vacuum to afford sodium 3-[3-(2-methyl-1,3,4-thiadiazol-5-ylthio)-prop-1-(t)-enyl]-7β-[α-(1H)-tetrazol-1-ylacetamido]-ceph-3-em-4-crboxylate, m.p. 190°–200° C. (decomp); uv($H_2O$):295 nm (ε 17,700); ir(KBr): 1765, 1675, 1610 $cm^{-1}$; nmr(DMSO-$d^6$) δ:2.65(3H,s); 3.43(2H,bs); 3.94(2H,d,J7Hz); 4.98(1H,m); 5.35(2H,s); 5.5(1H,m); 5.7(1H,m); 7.09(1H,d,J15Hz); 9.33(1H,s); 9.45(1H,m) ppm.

Similarly, sodium 3-[3-(3-methyl-1,2,4-thiadiazol-5-ylthio)-prop-1-(t)-enyl]-7β-[α-(1H)-tetrazol-1-ylacetamido]-ceph-3-em-4-carboxylate and sodium 3-[3-(2-methyl-1,3,4-oxadiazol-5-ylthio)-prop-1-(t)-enyl]-7β-[α-(1H)-tetrazol-1-ylacetamido]-ceph-3-em-4-carboxylate are prepared by following the same procedure using benzhydryl 3-[3-(3-methyl-1,2,4-thiadiazol-5-ylthio)-prop-1-(t)-enyl]-7β-amino-ceph-3-em-4-carboxylate and benzhydryl 3-[3-(2-methyl-1,3,4-oxadiazol-5-ylthio)-prop-1-(t)-enyl]-7β-amino-ceph-3-em-4-carboxylate as starting materials.

EXAMPLE 9

This example illustrates steps 5 and 6 of the first process described for preparing the compounds of the invention. In this example, a mixture of 0.08g. of benzhydryl 3-[3-(2-methyl-1,3,4-thiadiazol-5-ylthio)-prop-1-(t)-enyl]-7β-amino-ceph-3-em-4-carboxylate and 0.5 ml. of pyridine, in 10 ml. of chloroform, is stirred at 0° C. and then 0.1 ml. of phenoxyacetyl chloride is added, and the mixture stirred for 30 minutes. The mixture is then diluted with ethyl acetate and washed successively with dilute aqueous hydrochloric acid, dilute aqueous sodium bicarbonate solution and brine. The mixture is dried over anhydrous sodium sulfate, and then evaporated to dryness, under reduced pressure to afford benzhydryl 3-[3-(2-methyl-1,3,4-thiadiazol-5-ylthio)-prop-1-(t)-enyl]-7β-phenoxyacetamido-ceph-3-em-4-carboxylate.

A mixture of 70 mg. of the above obtained ester and 0.5 ml. of anisole is stirred at 0° C. and 2.5 ml. of trifluoroacetic acid is then added. The mixture is stirred vigorously for two minutes, then rapidly evaporated to dryness under reduced pressure. The resulting crude 3-[3-(2-methyl-1,3,4-thiadiazol-5-ylthio)-prop-1-(t)-enyl]-7β-(α-phenoxy-acetamido)-ceph-3-em-4-carboxylic acid residue is treated with ethyl ether, and affording solid which is then collected by filtration. The solid is dissolved in tetrahydrofuran, filtered, and the filtrate treated with an excess of a solution of sodium 2-ethylhexanoate in tetrahydrofuran. The mixture is evaporated to dryness. Isopropanol is added to the residue yielding a white solid, which separates, and is then collected by filtration, washed several times with isopropanol and dried under vacuum to afford sodium 3-[3-(2-methyl-1,3,4-thiadiazol-5-ylthio)-prop-1-(t)-enyl]-7β-(α-phenoxyacetamido)-ceph-3-em-4-carboxylate.

Similarly, sodium 3-[3-(3-methyl-1,2,4-thiadiazol-5-ylthio)-prop-1-(t)-enyl]-7β-(α-phenoxyacetamido)-ceph-3-em-4-carboxylate and sodium 3-[3-(2-methyl-1,3,4-oxadiazol-5-ylthio)-prop-1-(t)-enyl]-7β-(α-phenoxyacetamido)-ceph-3-em-4-carboxylate are prepared by following the same procedure using benzhydryl 3-[3-(3-methyl-1,2,4-thiadiazol-5-ylthio)-prop-1-(t)-enyl]-7β-amino-ceph-3-em-4-carboxylate and benzhydryl 3-[3-(2-methyl-1,3,4-oxadiazol-5-ylthio)-prop-1-(t)-enyl]-7β-amino-ceph-3-em-4-carboxylate as starting materials.

EXAMPLE 10

This example illustrates steps 5 and 6 of the first process described for preparing the compounds of the invention.

In this example, a solution of 0.26 g. of benzhydryl 3-[3-(2-methyl-1,3,4-thiadiazol-5-ylthio)-prop-1-(t)-enyl]-7β-amino-ceph-3-em-4-carboxylate in 15 ml. chloroform is treated with 0.15g. of trifluoromethylthioacetic acid and 0.25g. of dicyclohexylcarbodiimide. The mixture is stirred at room temperature for two hours and them filtered to remove dicyclohexylurea. The filtrate is evaporated to dryness to afford benzhydryl 3-[3-(2-methyl-1,3,4-thiadiazol-5-ylthio)-prop-1-(t)-enyl]-7-β-(α-trifluoromethylthioacetamido)-ceph-3-em-4-carboxylate.

A mixture of 200 mg. of the above obtained ester and 0.5 ml. of anisole is stirred at 0° C. and 2.5ml. of trifluoroacetic acid is then added. The mixture is stirred vigorously for two minutes, then rapidly evaporated to dryness under reduced pressure. The crude 3-[3-(2-methyl-1,3,4-thiadiazol-5-ylthio)-prop-1-(t)-enyl]-7β-(α-trifluoromethylthioacetamido)-ceph-3-em-4-carboxylic acid residue is treated with ethyl ether, and then filtered. The collected solid is dissolved in tetrahydrofuran, filtered, and the filtrate treated with an excess of a solution of sodium 2-ethylhexanoate in tetrahydrofuran. The mixture is evaporated to dryness. The residue is mixed with isopropanol and then filtered. The collected solid is washed several times with isopropanol and dried under vacuum affording sodium 3-[3-(2-methyl-1,3,4-thiadiazol-5-ylthio)-prop-1-(t)-enyl]-7β-(α-trifluoromethylthioacetamido)-ceph-3-em-4-carboxylate.

Similarly, sodium 3-[3-(3-methyl-1,2,4-thiadiazol-5-ylthio)-prop-1-(t)-enyl]-7β-(α-trifluoromethylthioacetamido)-ceph-3-em-4-carboxylate and sodium 3-[3-(2-methyl-1,3,4-oxadiazol-5-ylthio)-prop-1-(t)-enyl]-7β-(α-trifluoromethylthioacetamido)-ceph-3-em-4-carboxylate are prepared by following the same procedure using benzhydryl 3-[3-(3-methyl-1,2,4-thiadiazol-5-ylthio)-prop-1-(t)-enyl]-7β-amino-ceph-3-em-4-carboxylate and benzhydryl 3-[3-(2-methyl-1,3,4-oxadiazol-5-ylthio)-prop-1-(t)-enyl]-7β-amino-ceph-3-em-4-carboxylate as starting materials.

EXAMPLE 11

This example illustrates steps 5 and 6 of the first process described for preparing the compounds of the invention.

In this example, a solution of 0.25 g. of benzhydryl 3-[3-(2-methyl-1,3,4-thiadiazol-5-ylthio)-prop-1-(t)-enyl]-7β-amino-ceph-3-em-4-carboxylate and 0.15 g. of sydnon-3-acetic acid in ethyl acetate is treated with 0.24 g. of dicyclohexyl carbodiimide. The mixture is stirred for two hours at room temperature, then filtered and evaporated to dryness. The residue is subjected to thick-layer chromatography on silica gel eluting with acetone/dichloromethane, 1:10, affording benzhydryl 3-[3-(2-methyl-1,3,4-thiadiazol-5-ylthio)-prop-1-(t)-enyl]-7β-(α-sydnon-3-ylacetamido)-ceph-3-em-4-carboxylate.

A mixture of 0.15mg. of the above obtained ester and 0.5 ml. of anisole is stirred at 0° C. and 2.5 ml. of trifluoroacetic acid is then added. The mixture is stirred vigorously for two minutes, then rapidly evaporated to dryness under reduced pressure. The crude 3-[3-(2-methyl- 1,3,4-thiadiazol-5-ylthio)-prop-1-(t)-enyl]-7β-(α-sydnon-3-ylacetamido)-ceph-3-em-4-carboxylic acid residue is treated with ethyl ether, and filtered. The collected solid is dissolved in tetrahydrofuran, filtered, and the filtrate treated with an excess of a solution of sodium 2-ethylhexanoate in tetrahydrofuran. The mixture is evaporated to dryness. The residue is mixed with isopropanol and then filtered. The collected solid is washed several times with isopropanol and then dried under vacuum affording sodium 3-[3-(2-methyl-1,3,4-thiadiazol-5-ylthio)-prop-1-(t)-enyl]-7β-(α-sydnon-3-ylacetamido)-ceph-3-em-4-carboxylate.

Similarly, sodium 3-[3-(3-methyl-1,2,4-thiadiazol-5-ylthio)-prop-1-(t)-enyl]-7β-(α-sydnon-3-ylacetamido)-ceph-3-em-4-carboxylate and sodium 3-[3-(2-methyl-1,3,4-oxadiazol-5-ylthio)-prop-1-(t)-enyl]-7β-(α-sydnon-3-ylacetamido)-ceph-3-em-4-carboxylate are prepared by following the same procedure using benzhydryl 3-[3-(3-methyl-1,2,4-thiadiazol-5-ylthio)-prop-1-(t)-enyl]-7β-amino-ceph-3-em-4-carboxylate and benzhydryl 3-[3-(2-methyl-1,3,4-oxadiazol-5-ylthio)-prop-1-(t)-enyl]-7β-amino-ceph-3-em-4-carboxylate as starting materials.

EXAMPLE 12

This example illustrates steps 5 and 6 of the first process described for preparing the compounds of the invention. In this example, a solution of 0.1 g. of benzhydryl 3-[3-(2-methyl-1,3,4-thiadiazol-5-ylthio)-prop-1-(t)-enyl]-7β-amino-ceph-3-em-4-carboxylate in 5 ml. of acetone is stirred at 0° C. and a solution of 0.06gm. of 2-[(cyanomethyl)thio]acetyl chloride (prepared according to procedures described in U.S. Pat. No. 3,855,212) in 3 ml. of acetone, and a solution of 0.05gm. of triethylamine in 3ml. of acetone are added concurrently over a period of 15 minutes. The mixture is stirred at 5° C. for 1 hour and then diluted with ethyl acetate. The resulting solution is washed with dilute aqueous sodium bicarbonate and brine and then dried over anhydrous sodium sulfate and evaporated to dryness. The residual oil is chromatographed on silica gel eluting with acetone/dichloromethane 1:20, to afford benzhydryl 3-[3-(2-methyl-1,3,4-thiadiazol-5-ylthio)-prop-1-(t)-enyl]-7β-[2-{(cyanomethyl)thio}-acetamido]-ceph-3-em-4-carboxylate.

Trifluoroacetic acid (0.5 ml.) is added to a stirred mixture of 0.1 gm. of the above obtained ester and 0.5 ml. of anisole at 0° C. The mixture is stirred vigorously for two minutes and then evaporated to dryness under reduced pressure. The resulting crude 3-[3-(2-methyl-1,3,4-thiadiazol-5-ylthio)-prop-1-(t)-enyl]-7β-[2-{(cyanomethyl)thio}-acetamido]-ceph-3-em-4-carboxylic acid is dissolved in tetrahydrofuran, filtered, and the filtrate treated with an excess of a solution of sodium 2-ethylhexanoate in tetrahydrofuran. The mixture is evaporated to dryness and the residue is triturated with isopropanol and to yield a white solid which is then filtered. The collected solid is washed several times with isopropanol and dried under vacuum affording sodium 3-[3-(2-methyl-1,3,4-thiadiazol-5-ylthio)-prop-1-(t)-enyl]-7β-[2-{(cyanomethyl)thio}-acetamido]-ceph-3-em-4-carboxylate.

EXAMPLE 13

This example illustrates steps 5 and 6 of the first process described for preparing the compounds of the invention. In this example, a mixture of 0.25g. of benzhydryl 3-[3-(2-methyl-1,3,4-thiadiazol-5-ylthio)-prop-1-(t)-enyl]-7β-amino-ceph-3-em-4-carboxylate and 0.2 ml. of triethylamine are stirred in 5 ml. of methylene chloride at 0°-5° C. and a solution of 0.088 g. of syn-2-methoxyimino(fur-2-yl)acetyl chloride (prepared according to procedures described in U.S. Pat. No. 3,932,385) in 5 ml. of methylene chloride is then added. The mixture is stirred at room temperature for 2 hours, washed with dilute aqueous sodium bicarbonate and water and then dried over sodium sulfate and evaporated. The resulting residue is chromatographed on thick-layer silica gel plates, eluting with acetone/methylene chloride, 1:20 to afford benzhydryl 3-[3-(2-methyl-1,3,4-thiadiazol-5-ylthio)-prop-1-(t)-enyl]-7β-[2-methoxyimino-(fur-2-yl)acetamido]-ceph-3-em-4-carboxylate (syn isomer).

Trifluoroacetic acid (0.5 ml.) is added to a stirred mixture of 0.1 g. of the above obtained ester and 0.5 ml. of anisole at 0° C. The mixture is stirred vigorously for two minutes and then rapidly evaporated to dryness under reduced pressure. The resulting crude 3-[3-(2-methyl-1,3,4-thiadiazol-5-ylthio)-prop-1-(t)-enyl]-7β-[2-methoxyimino-(fur-2-yl)acetamido]-ceph-3-em-4-carboxylic acid(syn isomer) is dissolved in tetrahydrofuran and then filtered. The resulting filtrate is treated with an excess of a solution of sodium 2-ethylhexanoate in tetrahydrofuran and then evaporated to dryness. The resulting residue is triturated with isopropanol to yield a solid which is collected by filtration, washed with isopropanol and dried to afford sodium 3-[3-(2-methyl-1,3,4-thiadiazol-5-ylthio)-prop-1-(t)-enyl]-7β-[2-methoxyimino-(fur-2-yl)acetamido]-ceph-3-em-4-carboxylate.

EXAMPLE 14

This example illustrates step 7 of the first process described for preparing the compounds of the invention. In this example, 2.5 ml. of trifluoroacetic acid is added to a stirring mixture of 200 mg. of benzhydryl 3-[3-(2-methyl-1,3,4-thiadiazol-5-ylthio)-prop-1-(t)-enyl]-7β-amino-3-em-4-carboxylate and 0.5 ml. of anisole at 0° C. After three minutes, the mixture is evaporated to dryness and the resulting residue mixed with ethyl ether affording the crystalline trifluoroacetic acid salt of 3-[3-(2-methyl-1,3,4-thiadiazol-5-ylthio)-prop-1-(t)-enyl]-7β-amino-ceph-3-em-4-carboxylic acid which is then collected by filtration. The collected salt is mixed with 0.5 ml. water and 0.5 ml. of a 25% solution of a water immiscible polymeric amine (sold under the Trademark Amberlite LA-1 (acetate form) by the Rohm and Haas Company of Philadelphia, Pa.) in methylisobutyl ketone and stirred for one hour at room temperature. The mixture is then filtered and the product washed three times with 5 ml. of fresh methylisobutyl ketone and twice with 5 ml. of fresh ethyl acetate and then dried under vacuum affording 3-[3-(2-methyl-1,3,4-thiadiazol-5-ylthio)-prop-1-(t)-enyl]-7β-amino-ceph-3-em-4-carboxylic acid.

Similarly, 3-[3-(3-methyl-1,2,4-thiadiazol-5-ylthio)-prop-1-(t)-enyl]-7β-amino-ceph-3-em-4-carboxylic acid and 3-[3-(2-methyl-1,3,4-oxadiazol-5-ylthio)-prop-1-(t)-enyl]-7β-amino-ceph-3-em-4-carboxylic are prepared by following the same procedure using benzhydryl 3-[3-(3-methyl-1,2,4-thiadiazol-5-ylthio)-prop-1-(t)-enyl]-7β-amino-ceph-3-em-4-carboxylate and benzhydryl 3-[3-(2-methyl-1,3,4-oxadiazol-5-ylthio)-prop-1-(t)-enyl]-7β-amino-ceph-3-em-4-carboxylate as starting materials.

EXAMPLE 15

This example illustrates step 8 of the first process for preparing the compounds of the invention. In this example, 100 μl. of dichloroacetylmandeloyl chloride is added to a stirring mixture of 0.15 g. of 3-[3-(2-methyl-1,3,4-thiadiazol-5-ylthio)-prop-1-(t)-enyl]-7β-amino-ceph-3-em-4-carboxylic acid, 10 ml. of acetone and 0.2 ml. of 5%, wt., aqueous sodium bicarbonate solution at −20° C. The resulting mixture is stirred at −20° C. for 30 minutes and allowed to come to room temperature over a period of one hour. The solution is brought to pH 9 and maintained at that pH for 30 minutes; using 5%, wt., aqueous sodium carbonate solution as required. The aqueous phase is washed with ethyl ether, then acidified (pH2) using dilute aqueous hydrochloric acid, and extracted twice with ethyl acetate. The combined extracts are washed with brine, dried and evaporated to dryness in vacuo. The residue is mixed with a mixture of ethyl ether/hexane 1:1, by vol., and filtered and the collected solid washed again with ethyl ether/hexane 1:1, by vol., affording 3-[3-(2-methyl-1,3,4-thiaidazol-5-ylthio)-prop-1-(t)-3nyl]-7β-(α-hydroxy-α-phenylacetamido)-ceph-3-em-4-carboxylic acid.

Similarly, 3-[3-(3-methyl-1,2,4-thiadiazol-5-ylthio)-prop-1-(t)-enyl]-7β-(α-hydroxy-α-phenylacetamido)-ceph-3-em-4-carboxylic acid and 3-[3-(2-methyl-1,3,4-oxadiazol-5-ylthio)-prop-1-(t)-enyl]-7β-(α-hydroxy-α-phenylacetamido)-ceph-3-em-4-carboxylic acid are prepared by following the same procedure using 3-[3-(3-methyl-1,2,4-thiadiazol-5-ylthio)-prop-1-(t)-enyl]-7β-amino-ceph-3-em-4-carboxylic acid as starting materials.

EXAMPLE 16

This example illustrates step 8 of the first process described for preparing the compounds of the invention. In this example, 200 μl. of phenylacetyl chloride is added to a stirring mixture of 0.25 g. 3-[3-(2-methyl-1,3,4-thiadiazol-5-ylthio)-prop-1-(t)-enyl]-7β-amino-ceph-3-em-4-carboxylic acid, 10 ml. of acetone and 0.2 ml. of 5%, wt., aqueous sodium bicarbonate at −10° C.

The resulting mixture is stirred at −10° C. for 30 minutes and allowed to come to room temperature over a period of one hour. The mixture is then diluted with water, washed with ethyl ether, and then brought to pH 2 using dilute aqueous hydrochloric acid. The acidified mixture is extracted twice with ethyl acetate and the combined extracts washed with brine, dried and evaporated to dryness in vacuo affording a residue of crude 3-[3-(2-methyl-1,3,4-thiadiazol-5-ylthio)-prop-1-(t)-enyl]-7β-(α-phenylacetamido)-ceph-3-em-4-carboxylic acid.

Similarly, 3-[3-(3-methyl-1,2,4-thiadiazol-5-ylthio)-prop-1-(t)-enyl]-7β-(α-phenylacetamido)-ceph-3-em-4-carboxylic acid and 3-[3-(2-methyl-1,3,4-oxadiazol-5-ylthio)-prop-1-(t)-enyl]-7β-(α-phenylacetamido)-ceph-3-em-4-carboxylic acid are prepared by following the same procedure using 3-[3-(3-methyl-1,2,4-thiadiazol-5-ylthio)-prop-1-(t)-enyl]-7β-amino-ceph-3-em-4-carboxylic acid and 3-[3-(2-methyl-1,3,4-oxadiazol-5-ylthio)-prop-1-(t)-enyl]-7β-amino-ceph-3-em-4-carboxylic acid as starting materials.

EXAMPLE 17

This example illustrates step 8 of the first process described for the preparation of the compounds of the invention. In this example, a solution of 0.4 g. of D-(−)-α-sulfophenylacetyl chloride in 25 ml. of ethyl ether is added dropwise to an ice-cold stirring mixture of 0.28 g. of 3-[3-(2-methyl-1,3,4-thiadiazol-5-yl)-prop-1-(t)-enyl]-7β-amino-3-em-4-carboxylic acid and 10 ml. of 5%, wt., aqueous sodium bicarbonate. The mixture is stirred for one hour at 0° C. The aqueous layer is separated and washed with ethyl ether and brought to pH 1.5 by the addition of dilute aqueous hydrochloric acid and then extracted twice with ethyl acetate. The combined extracts are washed with brine, dried, and evaporated to dryness, in vacuo affording a crude residue of 3-[3-(2-methyl-1,3,4-thiadiazol-5-ylthio)-prop-1-(t)]-7β-(α-phenyl-α-sulfoacetamido)-ceph-3-em-4-carboxylic acid.

Similarly, 3-[3-(3-methyl-1,2,4-thiadiazol-5-ylthio)-prop-1-(t)-enyl]-7β-(α-phenyl-α-sulfoacetamido)-ceph-3-em-4-carboxylic acid and 3-[3-(2-methyl-1,3,4-oxadiazol-5-ylthio)-prop-1-(t)-enyl]-7β-(α-phenyl-α-sulfoacetamido)-ceph-3-em-4-carboxylic acid are prepared by following the same procedure using 3-[3-(3-methyl-1,2,4-thiadiazol-5-ylthio)]-7β-amino-ceph-3-em-4-carboxylic acid and 3-[3-(2-methyl-1,3,4-oxadiazol-5-ylthio)]-ceph-3-em-4-carboxylic acid as starting materials.

EXAMPLE 18

For purposes of purifying and isolating the free acids of the invention, a small portion (10 mg.) of each of the sodium salt products, prepared according to Examples 4A, 5, 6, 8, 9, 10, 11, 12 and 13, is respectively converted back to the 4-carboxylic acid by dissolving in water, adjusting the pH to 1.5 using dilute hydrochloric acid and extracting twice with ethyl acetate. The combined extracts are washed with brine, dried and evaporated to dryness. The residue is mixed with ethyl ether and the purified 4-carboxylic acid product collected by filtration.

EXAMPLE 19

This example illustrates methods of preparing the sodium salts of the invention. In this example, 60 mg. 3-[3-(2-methyl-1,3,4-thiadiazol-5-ylthio)-prop-1-(t)-enyl]-7β-(α-hydroxy-α-phenylacetamido)-ceph-3-em-4-carboxylic acid is dissolved in ethyl acetate and the sodium salt precipitated by the dropwise addition of a saturated solution of sodium 2-ethylhexanoate in ethyl acetate. The sodium salt is collected by filtration, washed twice with ethyl acetate and dried under vacuum to give the sodium salt of 3-[3-(2-methyl-1,3,4-thiadiazol-5-ylthio)-prop-1-(t)-enyl]-7β-(α-hydroxy-α-phenylacetamido)-ceph-3-em-4-carboxylic acid.

Similarly, by following the same procedure, the corresponding mono, and where applicable, bis, sodium salts of the products of Example 7, 14, 16 and 17 are respectively prepared.

EXAMPLE 20

This example illustrates step 1 of the second process described for preparing the compounds of the invention. In this example a solution of 3.2 g. of benzhydryl 3-(1-hydroxy-prop-2-enyl)-7β-(thiophen-2-ylacetamido)-ceph-2-em-4-carboxylate (obtained in Example 1) in 10 ml. of tetrahydrofuran and 10 ml. of acetic acid is stirred at 40° C. and 50 mg. of p-toluenesulfonic acid added. After stirring for six hours, the mixture is poured into water and extracted three times with ethyl acetate. The ethyl acetate extracts are combined and then sequentially washed with water, excess dilute aqueous sodium bicarbonate solution and brine, and then dried over anhydrous sodium sulfate. The dried mixture is evaporated to dryness under reduced pressure affording 3.1 g. of a yellow oil which is then chromatographed on silica gel eluting with dichloromethane/acetone 19:1. The homogeneous fractions, by thin-layer chromatography, are combined to give 1.5 g. of benzhydryl 3-[3-acetoxyprop-1-(t)-enyl)]-7β-(thiophen-2-ylacetamido)-ceph-2-em-4-carboxylate as a pale yellow oil; nmr (CDCl$_3$) δ: 1.98 (s, 3H); 3.82 (s, 2H); 4.43 (d, J 5.5 Hz, 2H); 5.22 (d, J 4.0 Hz, 1H); 5.25 (s, 1H); 5.52 (dd, J 4, 8 Hz, 1H); 5.68 (dt, J 5.5, 15 Hz, 1H); 6.18 (d, J 15 Hz, 1H); 6.30 (s, 1H; 6.65 d, J 8 Hz, 1H); 6.8-7.5 (m, 14H) ppm.

EXAMPLE 21

This example illustrates step 1a of the second process described for preparing the compounds of the invention. In this example a solution of 0.5 g. of benzhydryl 3-(1-hydroxy-prop-2-enyl)-7β-(thiophen-2-ylacetamido)-ceph-2-em-4-carboxylate in 10 ml. of tetrahydrofuran and 1 ml. of water is treated with about 50 mg. of p-toluenesulfonic acid and the resulting mixture stirred at room temperature. The reaction is monitored using thin-layer chromatography analysis. When the mole ratio of unrearranged 1-hydroxyprop-2-enyl compound (B) to 3-hydroxyprop-1-(t)-enyl compound (BE) is approximately 2:1 respectively, the mixture is diluted with water and extracted twice with ethyl acetate. The combined ethyl acetate extracts are washed with dilute aqueous sodium bicarbonate solution and then brine, dried over anhydrous sodium sulfate and evaporated to dryness under reduced pressure to give 0.45 g. of yellow oil. The oil is chromatographed on silica gel eluting with dichloromethane/acetone 9:1 to give 0.22 g. of benzhydryl 3-(1-hydroxyprop-2-enyl)-7β-(thiophen-2-ylacetamido)-ceph-2-em-4-carboxylate and 0.11 g. of benzhydryl 3-(3-hydroxyprop-1-(t)-enyl)-7β-(thiophen-2-ylacetamido)-ceph-2-em-4-carboxylate as a colorless oil; mnr (CDCl$_3$)δ; 3.79 (s, 2H); 3.96 (bd, J 5 Hz, 2H); 5.16 (d, J 4 Hz, 1H); 5.24 (bs, 1H); 5.52 (dd, J 4, 8.5 Hz, 1H); 5.71 (dt, J 5, 16 Hz, 1H); 6.11 (d, J 16 Hz, 1H); 6.22 (s, 1H); 6.7–7.5 (m, 15H) ppm.

EXAMPLE 22

This example illustrates step 1a' of the second process described for preparing the compounds of the invention. In this example a solution of 1.0 g. of benzhydryl 3-(1-hydroxy-prop-2-enyl)-7β-(thiophen-2-ylacetamido)-ceph-2-em-4-carboxylate in 5 ml. of pyridine is cooled to 0° C. and 4 ml. of acetic anhydride added. The mixture is allowed to stand at 0° C. for six hours, and then diluted with water and extracted twice with ethyl acetate. The combined extracts are washed with water, dilute aqueous hydrochloric acid, dilute aqueous sodium bicarbonate and brine, dried over anhydrous sodium sulfate and evaporated to dryness under reduced pressure affording 1.1 g. of a brown oil which is then chromatographed on silica gel eluting with dichloromethane/acetone 19:1. The thin-layer chromatography-pure fractions are combined affording 0.8 g. of benzhydryl 3-(1-acetoxyprop-2-enyl)-7β-(thiophen-2-ylacetamido)-ceph-2-em-4-carboxylate as a pale yellow oil;

Isomer A: oil, mnr (CDCl$_3$) δ: 1.91s, (3H; 3.82s, 2H); 4.95 (bs, 1H); 5.25 (d, J 4 Hz, 1H); 5.53 (dd, J4, 9 Hz, 1H); 5.0–5.9m; 6.36 (s, 1H); 6.39 (d, J 9 Hz, 1H); 6.7–7.5 (m, 14 H) ppm.

Isomer B: oil, nmr (CDCl$_3$) δ: 1.78 (s, 3H); 3.82 (s, 2H); 5.0–5.9m; 6.38 (s, 1H); 6.39 (d, J 9 Hz, 1H); 6.8–7.4 (m, 14H) ppm.

EXAMPLE 23

This example illustrates step 1b of the second process described for preparing the compounds of the invention. In this example 0.1 g. of benzhydryl 3-(3-hydroxyprop-1-(t)-enyl)-7β-(thiophen-2-ylacetamido)-ceph-2-em-4-carboxylate is dissolved in 2 ml. of pyridine and the solution then cooled to 0° C. and 2. ml. of acetic anhydride is added. The mixture is maintained at 0° C. for six hours, and then diluted with water and extracted twice with ethyl acetate. The combined ethyl extracts are washed with dilute aqueous sodium bicarbonate solution and brine, dried over anhydrous sodium sulfate and then evaporated to dryness under reduced pressure. The residue, a brown oil, is chromatographed on silica gel eluting with dichloromethane/acetone 19:1, affording 85 mg. of benzhydryl 3-(3-acetoxyprop-1-(t)-enyl)-7β-(thiophen-2-ylacetamido)-ceph-2-em-4-carboxylate as a pale yellow oil, identical to the sample described in Example 20.

EXAMPLE 24

This example illustrates step 1b' of the second process described for preparing the compounds of the invention. In this example a solution of 0.5 g. of benzhydryl 3-(1-acetoxyprop-2-enyl)-7β-(thiophen-2ylacetamido)-ceph-2-em-4-carboxylate in 10 ml. of tetrahydrofuran and 2 ml. of acetic acid is stirred at 40° C. and p-toluenesulfonic acid (50 mg.) then added. The mixture is stirred at 40° C. for four hours and then cooled to about 20° C. and diluted with water and extracted twice with ethyl acetate. The combined ethyl acetate extracts are washed with water, dilute aqueous sodium bicarbonate and brine, and dried over anhydrous sodium sulfate. Evaporating to dryness under reduced pressure gave 0.55 g. of a yellow oil. This was chromatographed on silica gel eluting with dichloromethane/acetone 19:1, giving 0.35 g. of benzhydryl 3-(3-acetoxyprop-1-(t)-enyl)-7β-(thiophen-2-ylacetamido)-ceph-2-em-4-carboxylate as a pale yellow oil, identical to the sample described in Example 20.

EXAMPLE 25

This example illustrates step 2 of the second process described for preparing the compounds of the invention. In this example a solution of 1.0 g. of benzhydryl 3-(3-acetoxyprop-1-(t)-enyl)-7β-(thiophen-2-ylacetamido)-ceph-2-em-4-carboxylate in 10 ml. of pyridine is cooled to 0° C. and five drops of triethylamine is added. The solution is allowed to stand at 0° C. for 24 hours and then diluted with water and extracted three times with ethyl acetate. The combined ethyl acetate extracts are washed with water, diluted aqueous hydrochloric acid, diluted aqueous sodium bicarbonate and brine, dried over anhydrous sodium sulfate and evaporated to dryness under reduced pressure to give 1.05 g. of a dark oil. This oil is chromatographed on silica gel eluting with benzene/ethyl acetate 9:1. Combination of thin-layer chromatography pure fractions gave 280 mg. of benzhydryl 3-(3-acetoxyprop-1-(t)-enyl)-7β-(thiophen-2-ylacetamido)-ceph-3-em-4-carboxylate, m.p. 162°–164° C., and 500 mg. of benzhydryl 3-(3-acetoxyprop-1-(t)-enyl)-7β-(thiophen-2-ylacetamido)-ceph-2-em-4-carboxylate. The recovered starting material is treated in the same manner as above, giving a further 150 mg. of benzhydryl 3-(3-acetoxy-prop-1-(t)-enyl)-7β-(thiophen-2-ylacetamido)-ceph-3-em-4-carboxylate, m.p. 162°-164° C.

EXAMPLE 26

This example illustrates step 2a of the second process described for preparing the compounds of the invention. In this example a solution containing 1.5 g. of benzhydryl 3-(3-acetoxyprop-1-(t)-enyl)-7β-(thiophen-2-ylacetamido)-ceph-2-em-4-carboxylate in 50 ml. of dichloromethane is stirred at 0° C. and m-chloroperbenzoic acid (0.5 g.) is added in portions over two hours. The mixture is evaporated to dryness and the residue dissolved in ethyl acetate and washed three times with dilute aqueous sodium bicarbonate solution and brine. The solution is dried over anhydrous sodium sulfate and evaporated to dryness under reduced pressure. On mixing with ethyl ether, the residue deposits a white solid which is collected by filtration and dried in vacuo to give 0.9 of benzhydryl 3-(3-acetoxyprop-1-(t)-enyl)-7β-(thiophen-2-ylacetamido)-ceph-3-em-4-carboxylate-1-oxide as a white crystalline solid, m.p. 209°-211° C.

EXAMPLE 27

This example illustrates step 2b of the second process described for preparing the compounds of the invention. In this example, a solution of 0.5 g. of benzhydryl 3-(3-acetoxyprop-1-(t)-enyl)-7β-(thiophen-2-ylacetamido)-ceph-3-em-4-carboxylate-1-oxide in 10 ml. of dimethylformamide was stirred under nitrogen at 0° C. and stannous chloride (0.5 g.) and acetyl chloride (1 ml.) are added. The mixture is stirred at 0° C. for 15 minutes and then at room temperature (about 20° C.) for 20 minutes. The mixture is then diluted with water and extracted three times with ethyl acetate. The combined ethyl acetate extracts are washed with brine, dried over anhydrous sodium sulfate and evaporated to dryness under reduced pressure to give 0.55 g. of a yellow oil. This oil is chromatographed on silica gel eluting with dichloromethane/acetone 19:1 affording 0.4 g. of benzhydryl 3-(3-acetoxyprop-1-(t)-enyl)-7β-(thiophen-2-ylacetamido)-ceph-3-em-4-carboxylate as a white crystalline solid, m.p. 162°-164° C.

EXAMPLE 28

This example illustrates step 3 of the second process described for preparing the compounds of the invention. In this example a solution of 200 mg. of benzhydryl 3-(3-acetoxy-prop-1-(t)-enyl)-7β-(thiophen-2-ylacetamido)-ceph-3-em-4-carboxylate in 5 ml. of dichloromethane is stirred at room temperature under nitrogen and 52 mg. of pyridine and 135 mg. of phosphorus pentachloride then added. The mixture is stirred at room temperature for three hours, then cooled to 0° C. and treated with 0.1 ml. of isobutanol. After stirring for one hour, 0.25 ml. of water is added and the mixture stirred vigorously for 15 minutes. The mixture is then diluted with excess dilute aqueous sodium bicarbonate solution and extracted twice with ethyl acetate. The combined ethyl acetate extracts is washed with brine, dried over anhydrous sodium sulfate and evaporated to dryness under reduced pressure, giving benzhydryl 3-(3-acetoxyprop-1-(t)-enyl)-7β-aminoceph-3-em-4-carboxylate as a brown oil, nmr (CDCl$_3$)δ: 1.99 (s, 3H); 3.55 (bd, 2H); 4.51 (d, J 6 Hz, 2H); 4.75 (d, J 5 Hz, 1H); 4.96 (d, J 5 Hz, 1H); 5.92 (dt, J 6, 16 Hz, 1H); 6.84 (d, J 16 Hz, 1H); 7.0–7.6 (m, 11H) ppm.

EXAMPLE 29

This example illustrates step 4 of the second process described for preparing the compounds of the invention. In this example a mixture of 0.1 g. of 3-(3-acetoxyprop-1-(t)-enyl)-7β-aminoceph-3-em-4-carboxylate, 0.2 g. of tetrazol-1-acetic acid and 0.2 g. of dicyclohexylcarbodiimide in 10 ml. of dichloromethane is stirred for two hours at room temperature, and then a solution of 0.2 g. of oxalic acid in 3 ml. of methanol is added. After 10 minutes, the mixture is filtered, and the solid washed with dichloromethane. The combined filtrate and washings are diluted with ethyl acetate and sequentially washed with dilute aqueous sodium bicarbonate solution, brine and dried over anhydrous sodium sulfate. The solution is then evaporated to dryness under reduced pressure affording a brown oil which is then purified using preparative thin-layer chromatography on silica gel developing with dichloromethane/acetone 19:1, affording benzhydryl 3-[3-acetoxyprop-1-(t)-enyl]-7β-(1H-tetrazol-1-ylacetamido)-ceph-3-em-4-carboxylate as a white solid, [α]$_D$ −64° (dioxane); uv (EtOH): 299 nm (ε16,100); ir(KBr): 1770, 1725, 1685 cm$^{-1}$; nmr (DMSO-d$_6$)δ: 1.94 (s, 3H); 3.65 (d, J 17 Hz, 1H); 3.92 (d, J 17 Hz, 1H); 4.52 (d, J 5 Hz, 2H); 5.25 (d, J 4.5 Hz, 1H); 5.41 (s, 2H, 5.85 dd, J 4.5, 9 Hz, 1H); 6.20 (dt, J 15, 5 Hz, 1H); 6.69 (d, J 15 Hz, 1H); 7.00 (s, 1H; 7.2–7.7 m, 10H); 9.39 (s, 1H; 9.59 d, J 9 Hz, 1H) ppm. Calcd. for C$_{28}$H$_{26}$N$_6$O$_6$S: C, 58.23; H, 4.56; N, 14.63. Found: C, 58.44; H, 4.78; N, 14.29.

EXAMPLE 30

This example illustrates step 4a of the second process described for preparing the compounds of the invention. In this example a mixture of 200 mg. of benzhydryl 3-(3-acetoxyprop-1-(t)-enyl)-7β-aminoceph-3-em-4-carboxylate and 0.5 ml. of anisole is stirred at 0° C. and 3 ml. of trifluoroacetic acid then added. The mixture is stirred for two minutes at 0° C. and then evaporated to dryness under reduced pressure. To the residue is added 0.5 ml. of water and 0.5 ml. of a 25% solution of Amberlite LA-1 (acetate form) in methylisobutylketone and the mixture is stirred at room temperature for one hour. The solid which separates is collected by filtration and washed with methylisobutylketone and acetone, and dried under vacuum affording 45 mg. of 3-[3-acetoxyprop-1-(t)enyl]-7β-aminoceph-3-em-4-carboxylic acid as a light brown powder which decomposes without melting; uv (H$_2$O); 292 nm (ε9,900); ir (KBr): 1805, 1735, 1625 cm$^{-1}$; nmr (CF$_3$CO$_2$D)δ: 2.25 (s, 3H); 3.73 (s, 2H); 4.90 (bd, J 5.5 Hz, 2H); 5.4 (m, 2H; 6.43 dt, J 5.5, 16 Hz, 1H); 7.61 (d, J 16 Hz, 1H) ppm.

The sodium salt of the acid is then prepared via treatment with sodium 2-ethylhexanoate as described in Example 31 hereinbelow to afford sodium 3-[3-acetoxyprop-1-(t)-enyl]-7β-aminoceph-3-em-4-carboxylate.

EXAMPLE 31

This example illustrates step 5 of the second process described for preparing the compounds of the invention. In this example a mixture of 95 mg. of benzhydryl 3-[3-acetoxyprop-1-(t)-enyl]-7β-(1H-tetrazol-1-ylacetamido)-ceph-3-em-4-carboxylate and 0.5 ml. of anisole is stirred vigorously at 0° C. and 3 ml. of trifluoroacetic acid added. After two minutes the mixture is evaporated to dryness under reduced pressure affording crude 3-[3-acetoxyprop-1-(t)-enyl]-7β-(1H-tetrazol-1-ylacetamido)-ceph-3-em-4-carboxylic acid as a residue, which is then dissolved in ethyl acetate and filtered. To the filtrate is added an excess of a solution of sodium 2-ethylhexanoate in isopropanol. The solid which separates is collected by filtration, washed with isopropanol and dried under vacuum affording sodium 3-[3-acetoxyprop-1-(t)-enyl]-7β-(1H-tetrazol-1-ylacetamido)-ceph-3-em-4-carboxylate as a white solid, which decomposes without melting; uv (H₂O): 292 nm (ε17,300); ir (KBr): 1775, 1740, 1700, 1600 cm⁻¹; nmr (DMSO-d₆) δ: 2.01 (s, 3H); 3.53 (bs, 2H); 4.55 (d, J 6 Hz, 2H); 5.06 (d, J 5 Hz, 1H); 5.40 (s, 2H; 5.58 dd, J 5, 9 Hz, 1H); 5.78 (dt, J 6, 16Hz; 1H); 7.08 (d, J 16 Hz, 1H); 9.39 (s, 1H); 9.53 (d, J 9 Hz, 1H) ppm.

EXAMPLE 32

This example illustrates step 6 of the second process described for preparing the compounds of the invention. In this example a mixture of 0.2 g. of benzhydryl 3-(3-acetoxyprop-1-(t)-enyl)-7β-(thiophen-2-ylacetamido)-ceph-3-em-4-carboxylate and 0.5 ml. of anisole is stirred at 0° C. and 2.5 ml. of trifluoroacetic acid then added. The mixture is stirred vigorously for two minutes at 0° C., and then evaporated to dryness under reduced pressure. The residue is mixed with ethyl ether affording 3-(3-acetoxyprop-1-(t)-enyl)-7β-(thiophen-2-ylacetamido)-ceph-3-em-4-carboxylic acid as a white solid which is then collected by filtration. The solid is dissolved in tetrahydrofuran, then filtered. The filtrate is treated with an excess of sodium 2-ethylhexanoate in tetrahydrofuran and then evaporated to dryness under reduced pressure. The residue was mixed with isopropanol, giving a white solid which is collected by filtration, washed twice with isopropanol and dried in vacuo to give 0.12 g. of sodium 3-(3-acetoxyprop-1-(t)-enyl)-7β-(thiophen-2-ylacetamido)-ceph-3-em-4-carboxylate as a white solid, which decomposes without melting; uv (H₂O): 292 nm (ε20,100); ir (KBr): 1765, 1740, 1663, 1620 cm⁻¹; nmr (DMSO-d₆)δ:1.97 (s, 3H); 3.44 (s, 2H); 3.73 (s, 2H); 4.53 (d, J 6 Hz, 2H); 4.98 (d, J 4.5 Hz, 1H); 5.48 (dd, J 4.5, 9 Hz, 1H); 5.65 (dt, J 6, 16 Hz, 1H); 6.8–7.0 (m, 2H; 7.06 d, 1H); 7.2–7.5 (m, 1H); 9.06 (bd, J 9 Hz, 1H) ppm.

EXAMPLE 33

This example illustrates step 7 of the second process described for preparing the compounds of the invention. In this example, a solution of 0.1 g. of sodium 3-(3-acetoxypropl-(t)-enyl)-7β-(thiophen-2-ylacetamido)-ceph-3-em-4-carboxylate, 200 mg. of 5-mercapto-2-methyl-1,3,4-thiadiazole and 100 mg. of sodium bicarbonate in 10 ml. water is stirred at 50° C. for eight hours. The mixture is cooled to room temperature, and the pH adjusted to 1.5 by the addition of dilute aqueous hydrochloric acid; the mixture is extracted twice with ethyl acetate. The combined ethyl acetate extracts are washed with brine, dried over sodium sulfate and evaporated to dryness under reduced pressure, affording 3-[3-(2-methyl-1,3,4-thiadiazol-5-ylthio)-prop-1-(t)-enyl]-7β-(thiophen-2-ylacetamido)-ceph-3-em-4-carboxylic acid. This is dissolved in 4 ml. of ethyl acetate, and an excess of sodium 2-ethylhexanoate in ethyl acetate is added. The resulting precipitate is collected by filtration, washed twice with isopropanol and dried under vacuum, giving sodium 3-[3-(2-methyl-1,3,4-thiadiazol-5-yl-thio)-prop-1-(t)-]-7β-thiophen-2-ylacetamido)-ceph-3-em-4-carboxylate.

Similarly, sodium 3-[3-(2-methyl-1,3,4-thiadiazol-5-ylthio)-prop-1-(t)-enyl]-7β-aminoceph-3-em-4-carboxylate and sodium 3-[3-(2-methyl-1,3,4-thiadiazol-5-ylthio)-prop-1-(t)-enyl]-7β-(1H-tetrazol-1-ylacetamido)-ceph-3-em-4-carboxylate can be prepared by the same procedure (steps 8 and 9 respectively) using the products of Examples 30 and 31, i.e., sodium 3-[3-acetoxyprop-1-(t)-enyl]-7β-aminoceph-3-em-4-carboxylate and sodium 3-[3-acetoxyprop-1-(t)-enyl]-7β-(1H-tetrazol-1-ylacetamido)-ceph-3-em-4-carboxylate as starting materials.

For purposes of purifying and isolating the free acids, a small portion (10 mg.) of the sodium salt product is converted back to the 4-carboxylic acid by dissolving the salt in water, adjusting the pH to 1.5 using dilute hydrochloric acid and extracting twice with ethyl acetate. The combined extracts are washed with brine, dried and evaporated to dryness. The residue is mixed with ethyl ether and the purified 4-carboxylic acid product collected by filtration.

Obviously, by substituting other appropriate acylating agents in steps 4 and 5a of the process exemplified in Examples 20–33, and by using 5-mercapto-2-methyl-1,3,4-thiadiazole, 5-mercapto-3-methyl-1,2,4-thiadiazole or 5-mercapto-2-methyl-1,3,4-oxadiazole in steps 7, 8 and 9 of this same process will be productive of the corresponding antibiotic agents of formula I.

What is claimed is:

1. A compound having the formula:

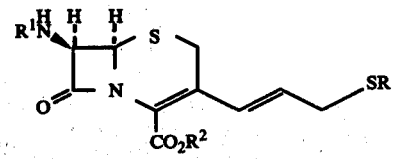

wherein:

R is 2-methyl-1,3,4-thiadiazol-5-yl, 3-methyl-1,2,4-thiadiazol-5-yl, or 2-methyl-1,3,4-oxadiazol-5-yl;

R¹ is a group having the formula:

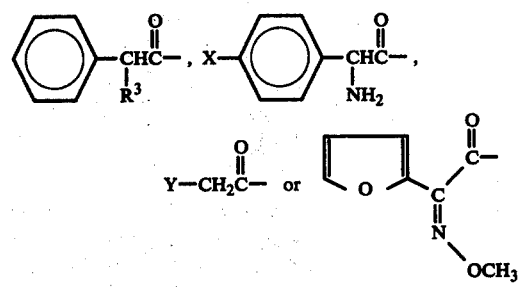

wherein R³ is hydrogen, hydroxy, sulfo or carboxy;

X is hydrogen or hydroxy; and Y is thiophen-2-yl, phenoxy, trifluoromethylthio, (1H)-tetrazol-1-yl, sydnon-3-yl or cyanomethylthio; and R² is hydrogen or a protecting group selected from the group of benzhydryl, benzyl, o-nitrobenzyl, p-nitrobenzyl, 3,5-dinitrobenzyl, p-methoxybenzyl, t-butyl, pivaloyloxymethyl, phenacyl and polyhaloalkyl having two to six carbon atoms; and pharmaceutically acceptable salts thereof when.

2. A compound of claim 1 having the formula:

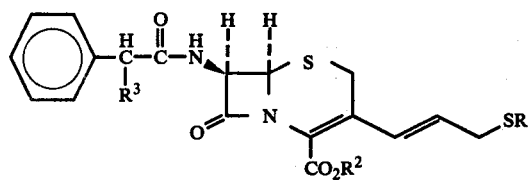

wherein R, $R^2$ and $R^3$ are as defined in claim 1, and the pharmaceutically acceptable salts thereof.

3. A compound of claim 2 wherein $R^2$ is benzhydryl.

4. A compound of claim 2 wherein $R^2$ is hydrogen and pharmaceutically acceptable salts thereof.

5. A compound of claim 4 wherein R is 2-methyl-1,3,4-thiadiazol-5-yl and $R^2$ is hydrogen or sodium.

6. A compound of claim 4 wherein R is 3-methyl-1,2,4-thiadiazol-5-yl.

7. The compound of claim 4 which is 3-[3-(3-methyl-1,2,4-thiadiazol-5-ylthio)-prop-1-(t)-enyl]-7β-(α-hydroxy-α-phenylacetamido)-ceph-3-em-4-carboxylic acid and pharmaceutically acceptable salts thereof.

8. The compound of claim 7 wherein said compound is a sodium salt.

9. A compound of claim 1 having the formula:

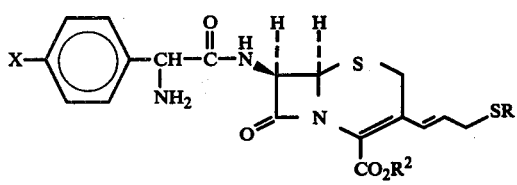

wherein R, $R^2$ and X are as defined in claim 1, and the pharmaceutically acceptable salts thereof.

10. A compound of claim 9 wherein $R^2$ is benzhydryl.

11. A compound of claim 9 wherein $R^2$ is hydrogen and pharmaceutically acceptable salts thereof.

12. A compound of claim 11 wherein R is 2-methyl-1,3,4-thiadiazol-5-yl and $R^2$ is hydrogen or sodium.

13. A compound of claim 1 having the formula:

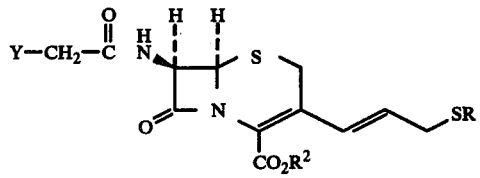

wherein R, $R^2$ and Y are as defined in claim 1, and the pharmaceutically acceptable salts thereof.

14. A compound of claim 13 wherein Y is thiophen-2-yl.

15. A compound of claim 13 wherein $R^2$ is benzhydryl.

16. The compound of claim 15 which is benzhydryl 3-[3-(2-methyl-1,3,4-thiadiazol-5-ylthio)-prop-1-(t)-enyl]-7β-(thiophen-2-ylacetamido)-ceph-3-em-4-carboxylate.

17. The compound of claim 15 which is benzhydryl 3-[3-(3-methyl-1,2,4-thiadiazol-5-ylthio)-prop-1-(t)-enyl]-7β-(thiophen-2-ylacetamido)-ceph-3-em-4-carboxylate.

18. The compound of claim 15 which is benzhydryl 3-[3-(2-methyl-1,3,4-oxadiazol-5-ylthio)-prop-1-(t)-enyl]-7β-(thiophen-2-ylacetamido)-ceph-3-em-4-carboxylate.

19. A compound of claim 18 wherein $R^2$ is hydrogen and pharmaceutically acceptable salts thereof.

20. The compound of claim 19 which is 3-[3-(2-methyl-1,3,4-thiadiazol-5-ylthio)-prop-1-(t)-enyl]-7β-(thiophen-2-ylacetamido)-ceph-3-em-4-carboxylic acid and pharmaceutically acceptable salts thereof.

21. The compound of claim 20 wherein said compound is a sodium salt.

22. The compound of claim 19 which is 3-[3-(3-methyl-1,2,4-thiadiazol-5-ylthio)-prop-1-(t)-enyl]-7β-(thiophen-2-ylacetamido)-ceph-3-em-4-carboxylic acid and the pharmaceutically acceptable salts thereof.

23. The compound of claim 22 wherein said compound is a sodium salt.

24. The compound of claim 19 which is 3-[3-(2-methyl-1,3,4-oxadiazol-5-ylthio)-prop-1-(t)-enyl]-7β-(thiophen-2-ylacetamido)-ceph-3-em-4-carboxylic acid and pharmaceutically acceptable salts thereof.

25. The compound of claim 24 wherein said compound is a sodium salt.

26. A compound of claim 20 wherein Y is trifluoromethylthio.

27. A compound of claim 26 wherein $R^2$ is benzhydryl.

28. A compound of claim 26 wherein $R^2$ is hydrogen and pharmaceutically acceptable salts thereof.

29. A compound of claim 28 wherein R is 2-methyl-1,3,4-thiadiazol-5-yl and $R^2$ is hydrogen or sodium.

30. A compound of claim 13 wherein Y is phenoxy.

31. A compound of claim 30 wherein $R^2$ is benzhydryl.

32. A compound of claim 30 wherein $R^2$ is hydrogen and pharmaceutically acceptable salts thereof.

33. A compound of claim 32 wherein R is 2-methyl-1,3,4-thiadiazol-5-yl and $R^2$ is hydrogen or sodium.

34. A compound of claim 13 wherein Y is (1H)-tetrazol-1-yl.

35. A compound of claim 34 wherein $R^2$ is benzhydryl.

36. A compound of claim 34 wherein $R^2$ is hydrogen and pharmaceutically acceptable salts thereof.

37. The compound of claim 36 which is 3-[3-(2-methyl-1,3,4-thiadiazol-5-ylthio)-prop-1-(t)-enyl]-7β-[α-(1H)-tetrazol-1-ylacetamido]-ceph-3-em-4-carboxylic acid and pharmaceutically acceptable salts thereof.

38. The compound of claim 37 wherein said compound is a sodium salt.

39. The compound of claim 36 which is 3-[3-(2-methyl-1,3,4-oxadiazol-5-ylthio)-prop-1-(t)-enyl]-7β-[α-(1H)-tetrazol-5-ylacetamido]-ceph-3-em-4-carboxylic acid and pharmaceutically acceptable salts thereof.

40. The compound of claim 39 wherein said compound is a sodium salt.

41. A compound of claim 13 wherein Y is sydnon-3-yl.

42. A compound of claim 41 wherein $R^2$ is benzhydryl.

43. A compound of claim 41 wherein $R^2$ is hydrogen and pharmaceutically acceptable salts thereof.

44. A compound of claim 43 wherein R is 2-methyl-1,3,4-thiadiazol-5-yl and $R^2$ is hydrogen or sodium.

45. A compound of claim 13 wherein Y is cyanomethylthio.

46. A compound of claim 46 wherein $R^2$ is benzhydryl.

47. A compound of claim 46 wherein $R^2$ is hydrogen and pharmaceutically acceptable salts thereof.

48. A compound of claim 47 wherein R is 2-methyl-1,3,4-thiadiazol-5-yl and $R^2$ is hydrogen or sodium.

49. A compound of claim 1 having the formula:

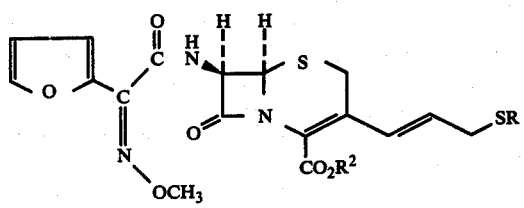

VI wherein R and $R^2$ are as defined in claim 1, and the pharmaceutically acceptable salts thereof.

50. A compound of claim 49 wherein $R^2$ is benzhydryl.

51. A compound of claim 46 wherein $R^2$ is hydrogen and pharmaceutically acceptable salts thereof.

52. The compound of claim 51 which is 3-[3-(2-methyl-1,3,4-thiadiazol-5-ylthio)-prop-1-(t)-enyl]-7β-[2-methoximino-(fur-2-yl)-acetamido]-ceph-3-em-4-carboxylic acid (syn isomer) and the pharmaceutically acceptable salts thereof.

53. The compound of claim 52 wherein said compound is a sodium salt.

54. A compound having the formula:

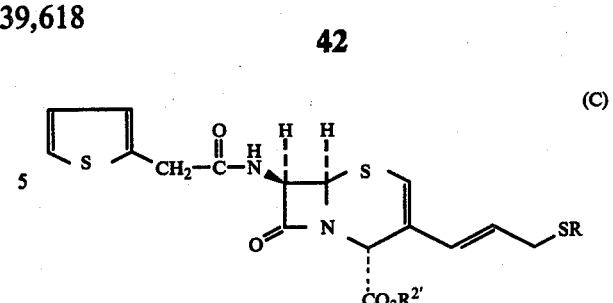

(C)

wherein:
R is 2-methyl-1,3,4-thiadiazol-5-yl, 3-methyl-1,2,4-thiadiazol-5-yl or 2-methyl-1,3,4-oxadiazol-5-yl; and
$R^{2'}$ is benzhydryl, benzyl, o-nitrobenzyl, p-nitrobenzyl, 3,5-dinitrobenzyl, p-methoxybenzyl, t-butyl, pivaloyloxymethyl, phenacyl, or polyhaloalkyl having two to six carbon atoms.

55. A compound of claim 54 wherein $R^{2'}$ is benzhydryl.

56. The compound of claim 55 which is benzhydryl 3-[3-(2-methyl-1,3,4-thiadiazol-5-ylthio)-prop-1-(t)-enyl]-7β-(thiophen-2-ylacetamido)-ceph-2-em-4-carboxylate.

57. The compound of claim 55 which is benzhydryl 3-[3-(3-methyl-1,2,4-thiadiazol-5-ylthio)-prop-1-(t)-enyl]-7β-(thiophen-2-ylacetamido)-ceph-2-em-4-carboxylate.

58. The compound of claim 55 which is benzhydryl 3-[3-(2-methyl-1,3,4-oxadiazol-5-ylthio)-prop-1-(t)-enyl]-7β-(thiophen-2-ylacetamido)-ceph-2-em-4-carboxylate.

59. An antibacterial composition comprising an effective amount of a compound of claim 1 wherein $R^1$ is other than hydrogen, or a pharmaceutically acceptable acid salt thereof, and mixtures of such compounds, with a suitable carrier.

* * * * *